United States Patent
Raghunathan

(10) Patent No.: US 11,213,681 B2
(45) Date of Patent: *Jan. 4, 2022

(54) HIGH FREQUENCY ELECTROSTIMULATION TREATMENT FOR RESTLESS LEGS SYNDROME OR PERIODIC LIMB MOVEMENT DISORDER

(71) Applicant: Noctrix Health, Inc., San Francisco, CA (US)

(72) Inventor: Shriram Raghunathan, San Jose, CA (US)

(73) Assignee: NOCTRIX HEALTH, INC., San Francisco, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 16/416,330

(22) Filed: May 20, 2019

(65) Prior Publication Data

US 2020/0108251 A1  Apr. 9, 2020

Related U.S. Application Data

(63) Continuation of application No. 16/196,863, filed on Nov. 20, 2018, now Pat. No. 10,342,977, which is a
(Continued)

(51) Int. Cl.
*A61N 1/36* (2006.01)
*A61B 5/0531* (2021.01)
(Continued)

(52) U.S. Cl.
CPC ........ *A61N 1/36057* (2013.01); *A61B 5/0531* (2013.01); *A61B 5/4082* (2013.01);
(Continued)

(58) Field of Classification Search
None
See application file for complete search history.

(56) References Cited

U.S. PATENT DOCUMENTS 5,487,759 A   1/1996  Bastyr et al.
5,725,471 A   3/1998  Davey et al.
(Continued)

FOREIGN PATENT DOCUMENTS

CN   110603073    12/2019
JP   2015512285    4/2015
(Continued)

OTHER PUBLICATIONS

"U.S. Appl. No. 16/196,863, Notice of Allowance dated Feb. 20, 2019", 8 pgs.
(Continued)

*Primary Examiner* — Kennedy Schaetzle
(74) *Attorney, Agent, or Firm* — Schwegman Lundberg & Woessner, P.A.

(57) ABSTRACT

Restless Leg Syndrome (RLS) or Periodic Limb Movement Disorder (PLMD) can be treated using high frequency (HF) electrostimulation. This can include selecting or receiving a subject presenting with RLS or PLMD. At least one electrostimulation electrode can be located at a location associated with at least one of, or at least one branch of, a sural nerve, a peroneal nerve, or a femoral nerve. HF electrostimulation can be delivered to the subject, which can include delivering subsensory, subthreshold, AC electrostimulation at a frequency that exceeds 500 Hz and is less than 15,000 Hz to the location to help reduce or alleviate the one or more symptoms associated with RLS or PLMD. A charge-balanced controlled-current HF electrostimulation waveform can be used.

27 Claims, 26 Drawing Sheets

Related U.S. Application Data continuation of application No. PCT/US2018/012631, filed on Jan. 5, 2018.

(60) Provisional application No. 62/442,798, filed on Jan. 5, 2017, provisional application No. 62/552,690, filed on Aug. 31, 2017.

(51) Int. Cl.

| | | |
|---|---|---|
| *A61B 5/00* | (2006.01) | |
| *A61N 1/08* | (2006.01) | |
| *A61N 1/04* | (2006.01) | |
| *A61B 5/11* | (2006.01) | |
| *A61N 1/05* | (2006.01) | |
| *A61B 5/08* | (2006.01) | |
| *A61B 5/024* | (2006.01) | |

(52) U.S. Cl.
CPC .............. *A61B 5/4836* (2013.01); *A61N 1/08* (2013.01); *A61N 1/36* (2013.01); *A61N 1/36014* (2013.01); *A61N 1/3614* (2017.08); *A61N 1/3615* (2013.01); *A61N 1/36031* (2017.08); *A61N 1/36034* (2017.08); *A61N 1/36067* (2013.01); *A61N 1/36139* (2013.01); *A61N 1/36167* (2013.01); *A61B 5/0022* (2013.01); *A61B 5/02405* (2013.01); *A61B 5/08* (2013.01); *A61B 5/1114* (2013.01); *A61B 5/1116* (2013.01); *A61B 5/4809* (2013.01); *A61B 5/4815* (2013.01); *A61B 5/7264* (2013.01); *A61B 5/7475* (2013.01); *A61B 2562/0219* (2013.01); *A61N 1/0456* (2013.01); *A61N 1/0476* (2013.01); *A61N 1/0484* (2013.01); *A61N 1/0492* (2013.01); *A61N 1/0556* (2013.01); *A61N 1/36021* (2013.01); *A61N 1/36071* (2013.01); *A61N 1/36078* (2013.01); *A61N 2001/083* (2013.01)

(56) References Cited

U.S. PATENT DOCUMENTS

| | | | |
|---|---|---|---|
| 5,759,198 | A | 6/1998 | Karell |
| 5,995,873 | A | 11/1999 | Rhodes |
| 6,001,861 | A | 12/1999 | Oertel et al. |
| 6,114,326 | A | 9/2000 | Schueler |
| 6,507,757 | B1 | 1/2003 | Swain |
| 6,602,868 | B2 | 8/2003 | McBrinn et al. |
| 7,403,821 | B2 | 7/2008 | Haugland et al. |
| 7,774,068 | B1 | 8/2010 | Lozano |
| 8,145,317 | B2 | 3/2012 | Demarais et al. |
| 8,365,741 | B2 | 2/2013 | Hennings et al. |
| 8,938,303 | B1 | 1/2015 | Matsen |
| 8,983,617 | B2 | 3/2015 | Chavan et al. |
| 9,017,273 | B2 | 4/2015 | Burbank et al. |
| 9,205,264 | B2 | 12/2015 | Heruth et al. |
| 9,302,046 | B1 | 4/2016 | Giuffrida et al. |
| 9,327,121 | B2 | 5/2016 | Thacker et al. |
| 9,387,338 | B2 | 7/2016 | Burnett |
| 9,452,287 | B2 | 9/2016 | Rosenbluth et al. |
| 9,504,827 | B2 | 11/2016 | DeGiorgio et al. |
| 9,561,371 | B2 | 2/2017 | Elborno |
| 9,566,470 | B2 | 2/2017 | Malizia |
| 9,604,056 | B2 | 3/2017 | Starr et al. |
| 9,610,448 | B2 | 4/2017 | Hou et al. |
| 9,656,070 | B2 | 5/2017 | Gozani et al. |
| 9,662,491 | B2 | 5/2017 | Yonce et al. |
| 9,662,502 | B2 | 5/2017 | Giuffrida et al. |
| 9,694,181 | B2 | 7/2017 | Bhadra et al. |
| 9,713,711 | B2 | 7/2017 | Hershey et al. |
| 9,737,709 | B2 | 8/2017 | Bachinski et al. |
| 9,750,933 | B2 | 9/2017 | Gregory et al. |
| 9,802,039 | B2 | 10/2017 | Palermo et al. |
| 9,802,041 | B2 | 10/2017 | Wong et al. |
| 9,808,627 | B2 | 11/2017 | Gliner et al. |
| 9,814,880 | B2 | 11/2017 | Hershey et al. |
| 10,195,425 | B2 | 2/2019 | Ostroff et al. |
| 10,342,977 | B2 * | 7/2019 | Raghunathan ..... A61N 1/36034 |
| 2003/0176822 | A1 | 9/2003 | Morgenlander |
| 2004/0093093 | A1 | 5/2004 | Andrews |
| 2006/0069415 | A1 | 3/2006 | Cameron et al. |
| 2006/0173074 | A1 | 8/2006 | Ellmen et al. |
| 2008/0262053 | A1 | 10/2008 | Reess |
| 2009/0062685 | A1 | 3/2009 | Bergethon et al. |
| 2009/0221943 | A1 | 9/2009 | Burbank et al. |
| 2010/0049111 | A1 | 2/2010 | Sorg |
| 2010/0160712 | A1 | 6/2010 | Burnett et al. |
| 2010/0191311 | A1 | 7/2010 | Scheiner |
| 2010/0249637 | A1 | 9/2010 | Walter et al. |
| 2011/0054573 | A1 | 3/2011 | Mitchell |
| 2012/0101358 | A1 | 4/2012 | Boettcher et al. |
| 2013/0325084 | A1 | 12/2013 | Lee |
| 2015/0066105 | A1 | 3/2015 | Elborno |
| 2015/0174002 | A1 | 6/2015 | Burbank et al. |
| 2015/0272815 | A1 | 10/2015 | Kitchens |
| 2016/0030280 | A1 | 2/2016 | Jones |
| 2016/0158542 | A1 | 6/2016 | Ahmed |
| 2016/0310741 | A1 | 10/2016 | Baru et al. |
| 2016/0354604 | A1 | 12/2016 | Kent |
| 2017/0157404 | A1 | 6/2017 | Moffitt et al. |
| 2017/0216586 | A1 | 8/2017 | Kent |
| 2019/0083784 | A1 | 3/2019 | Raghunathan |

FOREIGN PATENT DOCUMENTS

| | | |
|---|---|---|
| JP | 2016511651 | 4/2016 |
| JP | 2018526044 | 9/2018 |
| JP | 2020505099 | 2/2020 |
| WO | 2015095880 | 6/2015 |
| WO | 2015109023 | 7/2015 |
| WO | WO-2018/129351 | 7/2018 |
| WO | WO-2018129351 A1 | 7/2018 |

OTHER PUBLICATIONS

"International Application Serial No. PCT/US2018/012631, International Search Report dated May 30, 2018", 5 pgs.

"International Application Serial No. PCT/US2018/012631, Invitation to Pay Add'l Fees and Partial Search Report dated Mar. 27, 2018", 2 pgs.

"International Application Serial No. PCT/US2018/012631, Written Opinion dated May 30, 2018", 8 pgs.

"European Application Serial No. 18736570.5, Extended European Search Report dated Sep. 30, 2020", 7 pgs.

"International Application Serial No. PCT US2018 012631, International Preliminary Report on Patentability dated Jul. 18, 2019", 10 pgs.

"U.S. Appl. No. 17/241,924, Non Final Office Action dated Jul. 12, 2021".

"European Application Serial No. 18736570.5, Response filed Apr. 28, 2021 to Extended European Search Report dated Sep. 30, 2020", 26 pgs.

Allen, R P, "Restless Legs Syndrome/Willis-Eckbom Disease Pathophysiology", Sleep Med Clin. , 10(3), (2015), 207-214.

Clemens, S, et al., "Restless leg syndrome: revisiting the dopamine hypothesis from the spinal cord perspective", Neurology, 67, (2006), 7 pgs.

Kilgore, K. L, et al., "Nerve conduction block utilising high-frequency alternating current.", Med Biol Eng Comput., 42(3), (May 2004), 394-406.

Mitchell, U, "Medical devices for restless leg syndrome—clinical utility of the Relaxis pad", Ther & Clin Risk Management, (2015), 1789-1794.

Qing, K, et al., "Burst-Modulated Waveforms Optimize Electrical Stimuli for Charge Efficiency and Fiber Selectivity", IEEE Trans Neural Syst Rehabil Eng 23(6), (Nov. 2015), pp. 936-945.

Stewart, W, et al., "Prevalence and burden of overactive bladder in the United States", World J Urol, 20 327-336, (2003), 11 pgs.

(56) References Cited

OTHER PUBLICATIONS

"Japanese Application Serial No. 2019-537068, Notification of Reasons for Refusal dated Nov. 9, 2021", w English Translation, 15 pgs.

* cited by examiner

HIGH FREQUENCY ELECTROSTIMULATION TREATMENT FOR RESTLESS LEGS SYNDROME OR PERIODIC LIMB MOVEMENT DISORDER

CLAIM OF PRIORITY

This patent application is a continuation of U.S. patent application Ser. No. 16/196,863, filed Nov. 20, 2018, now issued as U.S. Pat. No. 10,342,977), which is a continuation of International Application Number PCT/US2018/012631 filed Jan. 5, 2018, which claims the benefit of priority of: (1) Shriram Raghunathan U.S. Provisional Patent Application No. 62/442,798, entitled "METHODS TO TREAT SYMPTOMS FROM OVERACTIVITY OF NERVES," filed on Jan. 5, 2017; and (2) Shriram Raghunathan U.S. Provisional Patent Application No. 62/552,690, entitled "SYSTEMS METHODS AND DEVICES TO MODULATE NERVE ACTIVITY TO TREAT NEUROLOGICAL DISORDER AND IMPROVE SLEEP QUALITY," filed on Aug. 31, 2017; each of which are incorporated by reference herein in their entirety and the benefit of priority of each of which is claimed.

TECHNICAL FIELD

This document pertains generally, but not by way of limitation, to medical diagnostic and treatment devices and methods, and more particularly, but not by way of limitation to Restless Legs Syndrome (RLS) or overactive nerve treatment.

BACKGROUND

Certain neurological disorders with bothersome symptoms can be attributed to overactivity of sensory or other peripheral nerve fibers, which can disrupt quality of life. In particular, Restless Legs Syndrome (RLS) and Periodic Leg Movement Disorder (PLMD) are two such neurological conditions that can significantly affect sleep in human patients. RLS (which can also be called Willis-Ekbom Disease (WED)) patients can experience uncomfortable tingling sensations in their lower limbs (legs). Such sensations can often be immediately relieved by moving the limb voluntarily, but doing so can interfere with the RLS patient's ability to fall asleep. PLMD patients can experience spontaneous movements of the lower legs during periods of sleep. This can cause the PLMD patient to wake up.

Burbank et al. U.S. Pat. No. 9,017,273, which issued on Apr. 27, 2015, is directed to devices and methods for treating restless legs syndrome, such as by providing a mechanical counterstimulation vibration having a frequency of between 50 Hz and 10 per minute.

Elborno U.S. Patent Publication 2015/0066105, which published on Mar. 5, 2015, is directed to devices and methods for treating essential tremor or restless leg syndrome using spinal cord stimulation.

Kent U.S. Patent Publication 2016/0354604, which published on Dec. 8, 2016, is directed to a method and apparatus for treating restless legs syndrome using stimulation of a sacral or lumbar region of the patient.

Matsen U.S. Pat. No. 8,938,303, which issued on Jan. 20, 2015, is directed to a restless leg therapeutic device, such as using a 25 Volt electricity generator to repeatedly cause constant muscle contractions. (See Matsen U.S. Pat. No. 8,938,303 at col. 6, lines 17-47.)

Lozano U.S. Pat. No. 7,774,068, which issued on Aug. 10, 2010, is directed to a system and method for treating movement disorders, including restless leg syndrome, such as using cortical brain stimulation.

For a patient diagnosed with primary RLS (e.g., RLS that is not secondary to some other primary co-morbidity, such as diabetes, neuropathy, etc., that may itself be separately treatable, in some cases), the first line of treatment may involve one or more of behavior changes, sleep changes, or exercise. The second line of treatment may involve dopaminergic therapy or iron level management, or both. The third line of treatment may involve one or more of anticonvulsants, off-label opiates, or benzodiazepines. In sum, the current treatments for RLS patients predominantly include pharmaceutical therapies, which can have serious side-effects.

SUMMARY

The present inventor has recognized that Restless Legs Syndrome (RLS) or Periodic Limb Movement Disorder (PLMD) can be treated using high frequency (HF) electrostimulation. This can include selecting or receiving a subject presenting with RLS or PLMD. At least one electrostimulation electrode can be located at a location associated with at least one of, or at least one branch of, a sural nerve, a peroneal nerve, or a femoral nerve. HF electrostimulation can be delivered to the subject, which can include delivering subsensory, subthreshold, alternating current (AC) electrostimulation at a frequency that exceeds 500 Hz and is less than 15,000 Hz to the location to help reduce or alleviate the one or more symptoms associated with RLS or PLMD. A charge-balanced controlled-current HF electrostimulation waveform can be used. The HF electrostimulation can be configured to be carried out without increasing blood flow to adjacent tissue.

The present inventor has discovered that, among other things, the HF subsensory and subthreshold electrostimulation waveform and techniques described herein can work better than low frequency transcutaneous electrical neurostimulation (TENS)—which can be sensed by the RLS patient, and which can actually make the RLS patient's symptoms more uncomfortable.

This Summary is intended to provide an overview of subject matter of the present patent application. It is not intended to provide an exclusive or exhaustive explanation of the invention. The Detailed Description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
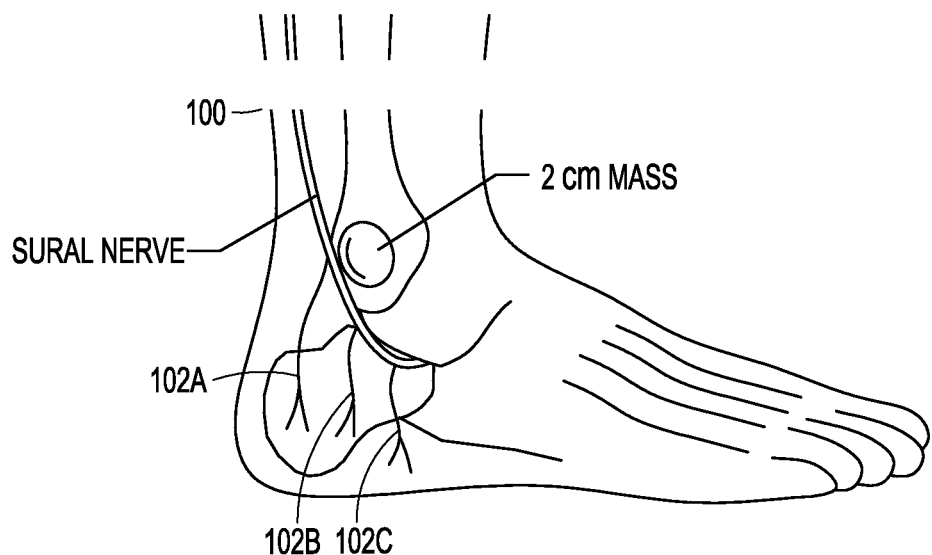
FIG. 1A illustrates an example of an ankle and foot region of a lower limb of a restless legs syndrome (RLS) patient, showing a targeted portion that can include a sural nerve or one or more of its branches.

Restless Legs Syndrome (RLS) or Periodic Limb Movement Disorder (PLMD) can be treated using high frequency (HF) electrostimulation. This can include selecting or receiving a subject presenting with RLS or PLMD. At least one electrostimulation electrode can be located at a location associated with at least one of, or at least one branch of, a sural nerve, a peroneal nerve, or a femoral nerve. HF electrostimulation can be delivered to the subject, which can include delivering subsensory, subthreshold, AC electrostimulation at a frequency that exceeds 500 Hz and is less than 15,000 Hz to the location to help reduce or alleviate the one or more symptoms associated with RLS or PLMD. A charge-balanced controlled-current HF electrostimulation waveform can be used.

Pathophysiology of RLS

RLS pharmaceutical treatments can include dopamine supplementation (e.g., levodopa), dopamine agonists (e.g., ropinirole, pramipexole), or anticonvulsants (e.g., gabapentin), in certain cases. Mechanical vibration pad approaches are believed not efficacious or better than placebo. A large number of RLS patients can suffer from augmentation of the RLS disease, which is a side-effect of some RLS drugs, and which can cause symptoms of the RLS disease to no longer be in the lower limbs or confined to periods of rest and sleep only. As a result, a number of these RLS augmentation patients can end up on sleep medications or opiates to manage their condition, with possible additional side-effects.

The underlying pathophysiology that causes people to develop RLS may be hypothesized to involve a central dopamine deficiency. The dramatic and immediate treatment benefits from levodopa may lead to a view that RLS patients may have a significant brain dopamine deficiency. The search to document the dopamine abnormalities in RLS is more difficult than expected and yields surprising results. Initial cerebrospinal fluid (CSF) analyses showed no differences between RLS patients and control patients for the major proteins related to dopamine. A repeat analysis of 3-orthymethyl dopamine (3-OMD) indicated significant increases within the CSF in 2 independent samples (See Allen, Connor, & Hyland, 2009). Moreover, the increases correlated with the dopamine metabolite, homovanillic acid (HVA). Given the metabolic pathways from tyrosine hydroxylase to dopamine, the increase in both 3-OMD and HVA may be best explained as an increase in tyrosine hydroxylase activity leading to increased dopamine production.

A problem arises: if in the RLS patient's brain dopamine is already abnormally increased, how does increasing this further by administering levodopa reduce the symptoms? Resolving this apparent contradiction may involve recognizing that there is a strong circadian aspect of both dopaminergic activity and
RLS symptoms. Increased dopaminergic stimulation can produce a postsynaptic downregulation, likely at both receptor and internal cellular function. A general pattern of decreased D2 receptors, especially for the more severe RLS cases, may represent part of this down-regulation of response. But dopamine has a clear circadian activity pattern, decreasing in the evening and night, and increasing in the morning. The RLS postsynaptic adjustment to increased dopamine stimulation may suffice for the daytime, but seems to overcompensate when dopamine levels are
lower during the evening and night. This may produce a relative evening and nighttime dopamine deficit, despite an overall dopamine increase. Thus, there is a circadian pattern of evening and night RLS symptoms with, if anything, hyperalertness and arousal in the morning that may prevent the expected sleepiness for the short and disrupted RLS sleep episode.

In sum, RLS pathophysiology can occur in a wide range of locations and systems and may have multiple pathways to disease. Pathophysiologic findings for RLS may help guide treatment advances for reducing the risk of dopamine augmentation and emphasizing the importance of developing better methods to manage RLS symptoms.

Pharmacological Treatments for RLS

Dopaminergic agents can be a first-line pharmacological therapy for RLS. Patients with serum ferritin values in the low-to-normal range may benefit from iron supplementation, as may difficult-to-treat RLS patients on dopaminergic treatment, in whom iron supplementation may inhibit or reduce RLS augmentation (Trenkwalder & Paulus, 2010).

Dopaminergic therapy for RLS can include dopamine agonists, but levodopa was the first dopaminergic agent used for RLS. Dopamine agonists may be superior to levodopa with respect to efficacy parameters, and less RLS augmentation may occur with these drugs than with levodopa. However, the dopaminergic adverse-effect profile, which can include nausea, blood pressure decrease, or dizziness, may be less severe with levodopa. Limitations of levodopa may lie both in its lack of efficacy and in RLS augmentation, the latter of which occurred in 50-70% of RLS patients in long-term observational studies. Table 1 below shows a list of dopaminergic medications for RLS treatment.

TABLE 1

Dopaminergic medications for RLS treatment

| Medication | Daily Dose Rate | Possible Side Effects |
| --- | --- | --- |
| Levodopa/dopa-decarboxylase inhibitor | 100/25-400/100 mg | Diarrhea, nausea, dyspepsia, reduced general drive, muscle weakness, somnolence, headache |
| Pramipexole | 0.125-0.75 mg | Nausea, dizziness, fatigue, somnolence, headache, orthostatic hypotension |
| Ropinirole | 0.25-4 mg | Nausea, dizziness, fatigue, somnolence, headache, orthostatic hypotension |
| Rotigotine (transdermal patches) | 1-3 mg | Nausea, dizziness, fatigue, somnolence, headache, orthostatic hypotension. |
| Cabergoline | 0.5-2.0 mg | Nausea, dizziness, fatigue, somnolence, headache, orthostatic hypotension, cardiac valvular disease |
| Pergolide | 0.25-0.75 mg | Nausea, dizziness fatigue, somnolence, headache, orthostatic hypotension, cardiac valvular disease |

Electrostimulation Treatment of RLS

The present techniques can include electrostimulation treatment of RLS or PLMD. The present techniques can include one or more specified selected nerve targets, such as a sural nerve, a peroneal nerve, or a femoral nerve, which the present inventor has recognized to be particularly useful electrostimulation target locations for RLS or PLMD. RLS symptoms are most commonly reported to originate in the lower legs for most patients. Specifically, the RLS symptoms affect the anterior tibialis region in the front and the gastrocnemius muscle region in the back. Without being bound by theory, the overactivity of sensory nerve afferents emerging from these regions of innervation likely cause the symptoms to go away temporarily when these muscles activate (e.g., when the leg is moved). The superficial peroneal nerve and its direct peripherally extending branches and the sural nerve and its direct peripherally extending branches are the primary sensory nerves innervating this region of the leg. Therefore, such nerve locations are prime targets for RLS electrostimulation therapy.

In RLS or PLMD patients reporting symptoms that originate in the upper leg, the femoral nerve and its direct peripherally extending branches carry most of the sensory innervation back from the rectus femoris muscle and the biceps femoris on the back of the leg. Therefore, the femoral nerve provides an additional target location for RLS electrostimulation.

Peroneal Nerve Location Example

Figure 1B:
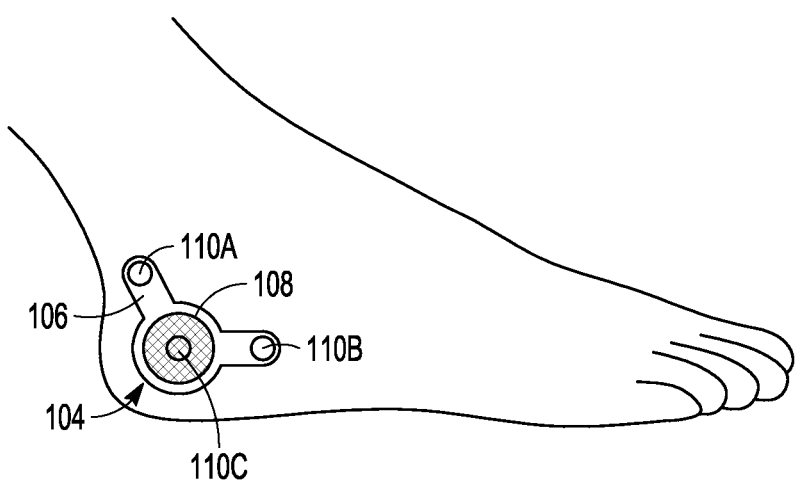
FIG. 1B illustrates an example of a wearable external electrostimulation device shown located in close proximity to the targeted sural nerve or its branches.
Figure 1C:
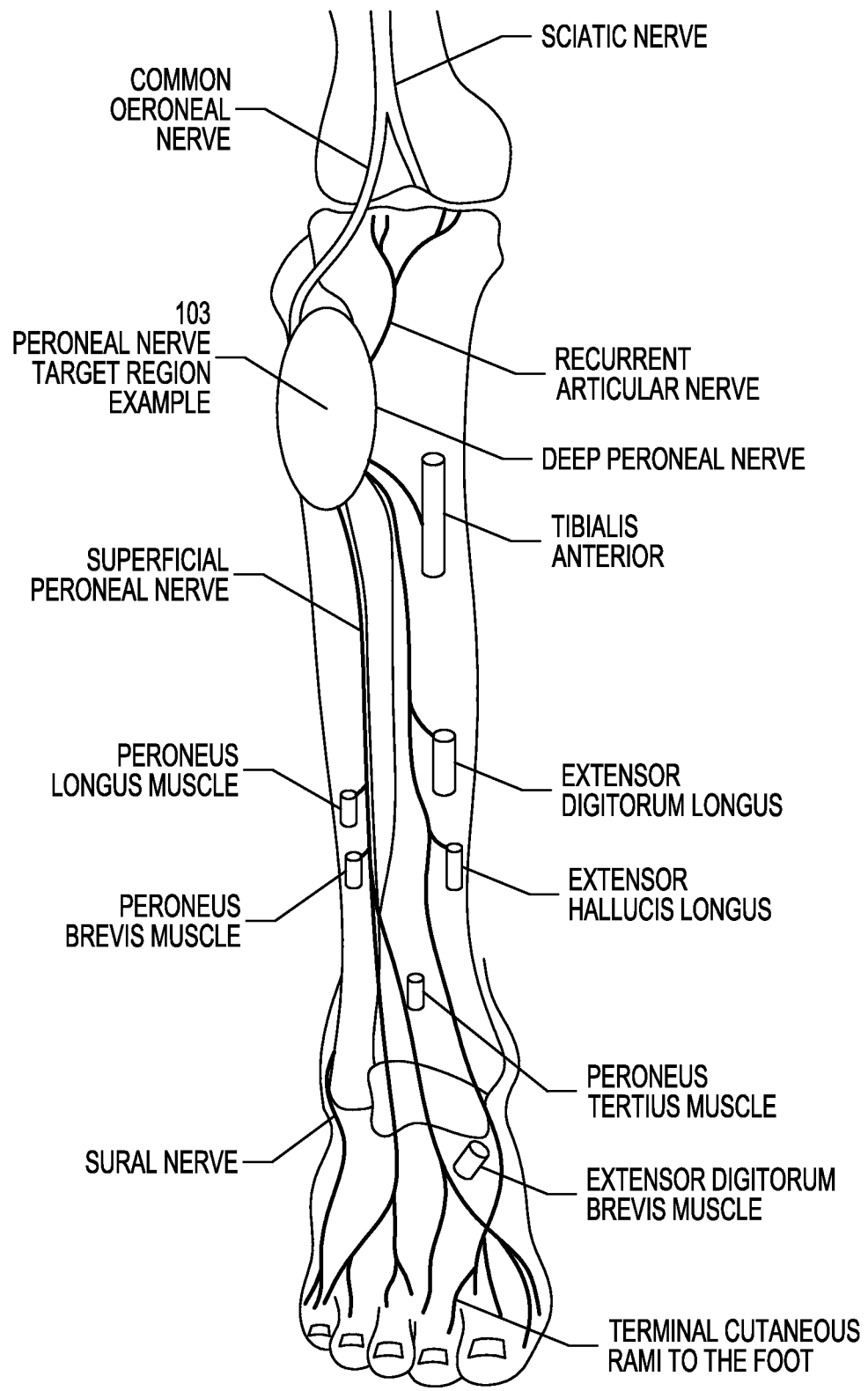
FIG. 1C illustrates an example of the wearable external electrostimulation device shown located in close proximity to a targeted region of a targeted peroneal nerve.

At the peroneal nerve target location, at least one electrode can be placed, such as preferably externally on the skin directly above or as close to possible to the superficial peroneal nerve (FIG. 1C). At least one electrode can be located directly below the bone landmark of the fibula in the outside of the knee below the lateral collateral ligament, or within 1 to 2 inches of the same. A second electrode may be located such that there is at least 1 inch of separation from the edge of the first electrode to the edge of the second electrode. The second electrode can be placed either along the length of the peroneal nerve, e.g., further down the leg, or the second electrode can be placed directly over the tibia, such as at about 1 to 2 inches below the first electrode. In an example, this second electrode can be located directly opposing the first electrode, to the inside of the knee, directly below the medial collateral ligament on the side of the tibia. The electrostimulation field may then be varied, such as to extend between a smaller or longer distance, such as to decrease sensory perception by the patient, if desired.

In an example, two separate or different electrostimulation fields can be applied, such as by using the second electrode on the tibia as the common return electrode, such as can create a modulated electrostimulation field across the leg below the knee.

Sural Nerve Location

At the sural nerve location, at least one electrode can be placed, such as preferably externally on the skin directly above, or as close to possible to the sural nerve, such as at a location between the lateral malleolus and calcaneus on the outside of the subject's foot. As shown in FIG. 1B, multiple electrodes can be located along the length of a portion of the sural nerve, such as with one electrode that can be located directly behind the 2 cm bony mass of the lateral malleolus. One or more additional electrodes can also be provided, such as can be respectively included on two extended "wings" that can be about 1.0 to 1.5 inches laterally spread from the central electrode, such as can form a 90 degree to 180 degree angle with the central electrode, such as to locate these additional electrodes along the length of the sural nerve, for example, a first additional electrode can be located at adjacent to the calcaneal tendon and a second additional electrode can be located above the base of the lateral longitudinal arch on the outside of the foot.

Femoral Nerve Location

At the femoral nerve location, at least one electrode can be placed, such as preferably externally on the skin directly above, or as close to possible to the femoral nerve, such as at a location at the approximate center of the "femoral triangle" that is bordered by the inguinal ligament on the superior side, the sartorius muscle on the lateral side, and the adductor longus on the medial side. In examples that can include multiple electrodes, such additional electrodes may be located with a minimum of 1 inch separation to the first electrode, from electrode edge to electrode edge, and can be arranged for placement along the length of the femoral nerve.

The present techniques can additionally or alternatively include electrostimulation that can be specially configured to preferentially activate certain nerve fibers over others, such as to inhibit, treat, reduce, prevent, or avoid one or more RLS symptoms. The electrostimulation can be specially configured to be subsensory (e.g., not noticeable enough to affect the patient's ability to fall asleep or stay asleep). The electrostimulation can be specially configured to be subthreshold (e.g., to avoid muscle activation in the patient, which could also interfere with the patient's ability to fall asleep or stay asleep). The electrostimulation can be configured very differently than traditional low frequency sensory transcutaneous electrical nerve stimulation (TENS), which can be ineffective or can even exacerbate RLS symptoms, thereby worsening the RLS patient's ability to fall asleep. The present techniques can be applied in an open-loop fashion, can allow patient control or titration, or can include closed-loop operation, such as can be based upon one or more sensed or received physiological parameters, such as sleep-state, or the like.

FIG. 1A illustrates an example of an ankle and foot region of a lower limb of an RLS patient, showing a sural nerve 100 and its branches 102A, 102B, 102C, such as can be specifically targeted by locating an electrostimulation device in close proximity thereto, such as for delivering an electrostimulation that can be configured to inhibit, reduce, or eliminate an RLS symptom.

FIG. 1B illustrates an example of a wearable external electrostimulation device 104 shown located in close proximity to the targeted sural nerve 100 or its branches 102A-C, such as for delivering a transcutaneous electrical stimulation thereto. In this example, the electrostimulation device 104, such as can include an adhesive patch 106, such as can carry an electronics unit 108 such as with separate or integrated electrodes 110A-B that can be electrically connected to the electronics unit 108. FIG. 1B shows electrodes 110A-B located separately on the adhesive patch 102 from the electronics unit 108, however, one or both of the electrodes 110A-B (or an additional electrode 110C (not shown) can be located on a patient-facing portion of the electronics unit 108, such as can be left exposed to the patient's skin by an opening in the adhesive patch 106. In an example, the electrostimulation device 104 can be adhered to or otherwise affixed or stabilized at a location on a lateral or medial surface of the foot, such as upon the posterolateral side of the leg near the dorsal aspect of the lateral side of the foot, such as toward the heel and behind and adjacent to a condylar surface of the ankle.

FIG. 1C illustrates an example of the wearable external electrostimulation device 104 shown located in close proximity to a targeted region 103 of a targeted peroneal nerve, such as at an anterior or lateral location just below the subject's knee, such as over a portion of the deep peroneal nerve. The wearable external electrostimulation device 104 can be alternatively or additionally located at an even more inferiorly-located region on the lower leg, such as over a portion of a superficial peroneal nerve, such as can innervate one or more parts of the tibialis anterior muscle.

Figure 1D:
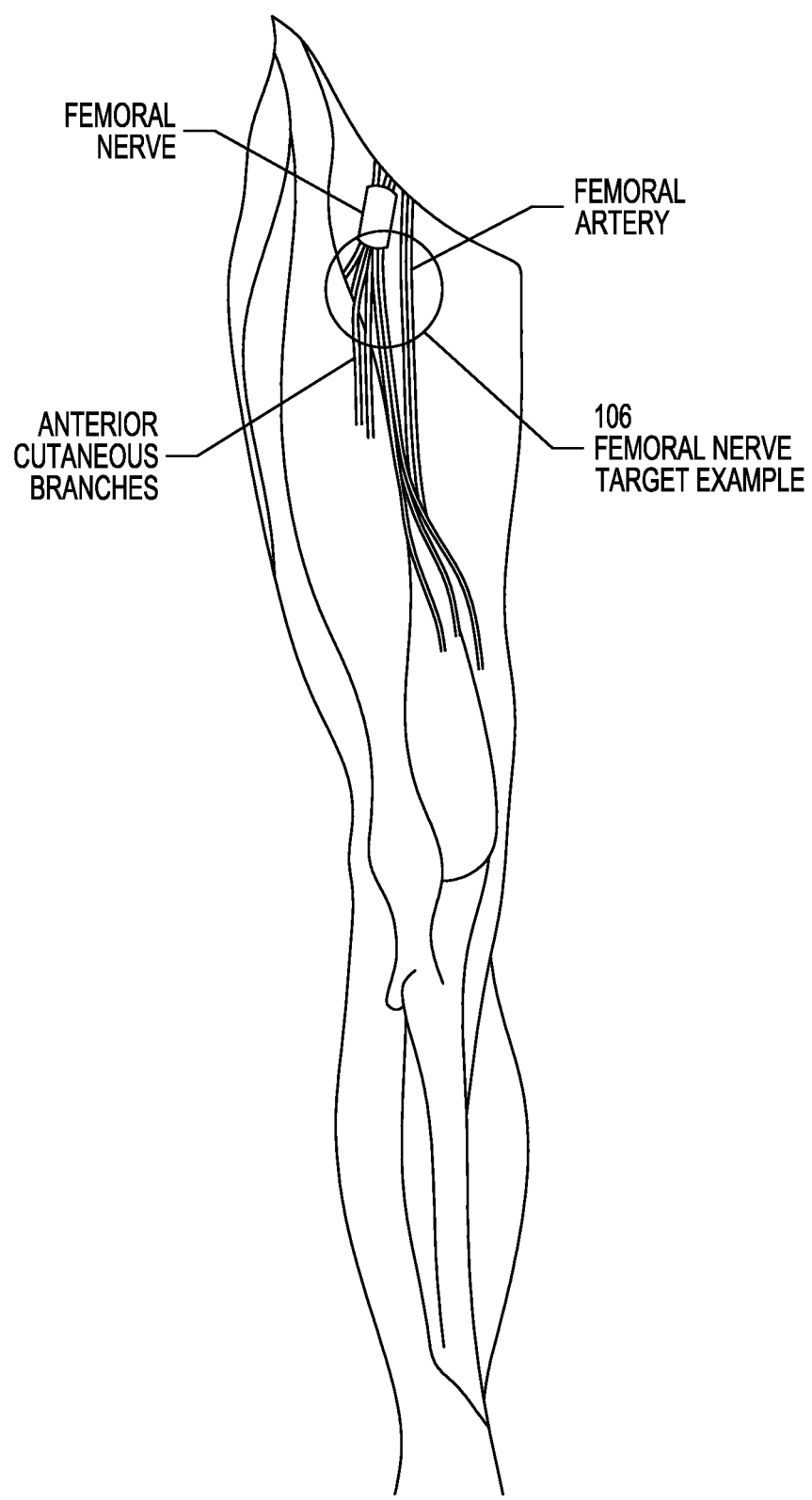
FIG. 1D illustrates an example showing how the wearable external electrostimulation device can be located in close proximity to a targeted region of a targeted femoral nerve.

FIG. 1D illustrates an example showing how the wearable external electrostimulation device can be located in close proximity to a targeted region 106 of a targeted femoral nerve, such as at an anterior upper thigh region or above the knee at an anterior and slightly more medial location.

At any of the desired target locations, the electrostimulation device 104 can be additionally or alternatively localized using a wearable component or garment, for example, such as with the electrostimulation device 104 carried by compression shorts or leggings, compression knee brace, ankle brace, sock, legging, sleeve, or the like.

Figure 2:
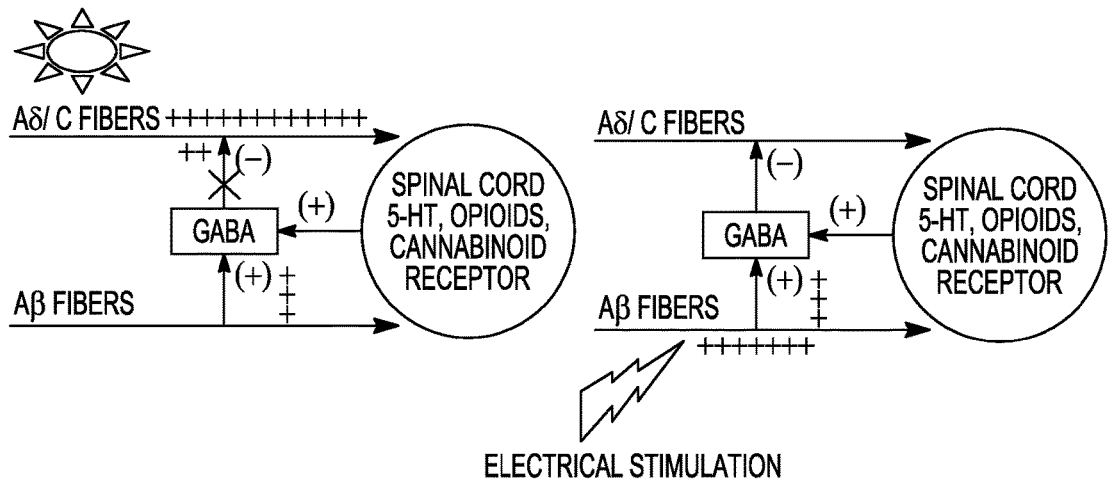
FIG. 2 shows an example of a particular mechanism of action that can be specifically targeted by delivering a tailored electrostimulation, such as described herein, such as to a specifically targeted location.

FIG. 2 shows an example of a particular mechanism of action that can be specifically targeted by delivering a tailored electrostimulation, such as described herein, such as to a specifically targeted location. But as an initial matter, it is worth noting that peripheral nerves are made up of a bundle of sub-types of nerves, such as can be classified as type A, B, or C, such as based on their respective conduction velocities and diameter, such as summarized in Table 2.

TABLE 2

Nerve Fiber Types and Characteristics

| Type of Nerve Fiber (Lloyd's) | Information | Myelin-ated? | Diameter (microm-eters) | Conduction Velocity (m/s) |
| --- | --- | --- | --- | --- |
| A-alpha (or "Type I") | Proprioception | Yes | 13-20 | 80-120 |
| A-Beta (or "Type II") | Touch | Yes | 6-12 | 35-90 |
| A-Delta (or "Type III") | Pain (Mechanical and Thermal) | Yes | 1-5 | 5-40 |
| C (or "Type IV") | Pain (Mechanical, thermal, chemical) | No | 0.2-.5 | 0.5-2 |

The A-alpha and A-beta nerve fibers are some of the largest in diameter, and can be targeted and recruited by lower amplitudes of electrostimulation, and are some of the fastest conducting nerve fibers, as evidenced by their reported conduction velocities as summarized in Table 2.

Without being bound by theory, it is believed that alleviating RLS symptomology can benefit from electrostimulation that can be specifically tailored, such as to preferentially recruit one or more types of nerve fibers at the specifically targeted location, such as explained with respect to FIG. 2, such as one of a sural nerve, peroneal nerve, femoral nerve locations, or a nerve branch extending peripherally therefrom.

In FIG. 2, the left-hand side illustrates the situation believed to exist in a symptomatic RLS patient. The RLS symptoms are believed to be caused by irritated or overactive Alpha-delta and C fibers that may cause ectopic neural activity that is interpreted as sensations of discomfort, which can be modulated by a spinal cord 5-HT, opioid or cannabinoid receptor, which, in turn, can be affected by preferentially recruiting (e.g., stimulating nerve fiber activity in) Alpha-beta fibers that release inhibitory neurotransmitters (GABA) to suppress this ectopic activity pattern.

In FIG. 2, the right-hand side illustrates the situation believed to exist when an electrostimulation is appropriately tailored and delivered to an appropriate target location (e.g., to one or more of a sural, peroneal, or femoral nerve to one or more peripherally extending branches thereof). The tailored electrostimulation at one or more of these particularly selected target nerve locations (e.g., one or more of a sural, peroneal, or femoral nerve to one or more peripherally extending branches thereof) can active faster-conducting Alpha-beta fibers, which, in turn, can stimulate production of GABA by the spinal cord 5-HT, opioid or cannabinoid receptor, which, in turn can calm the slower-conducting Alpha-Delta or C fibers inhibiting overactivity or irritating impulses from being generated and conducted by the Alpha-Delta or C fibers.

One technique for assessing efficacy of treatment of RLS symptoms is to perform a suggested immobilization test (SIT). In the present case, the SIT test can be performed before administering therapy, and then continued or performed again during or after administering therapy. As part of the SIT, patients can be asked to sit upright on a bed with legs stretched outward, such as for a duration of 60 minutes, with leg movements recorded (e.g., using an accelerometer or other leg-movement sensor) and asked to score their discomfort, such as on a scale of 0 to 10, every 10 minutes for the entire 60-minute duration.

Figure 3:
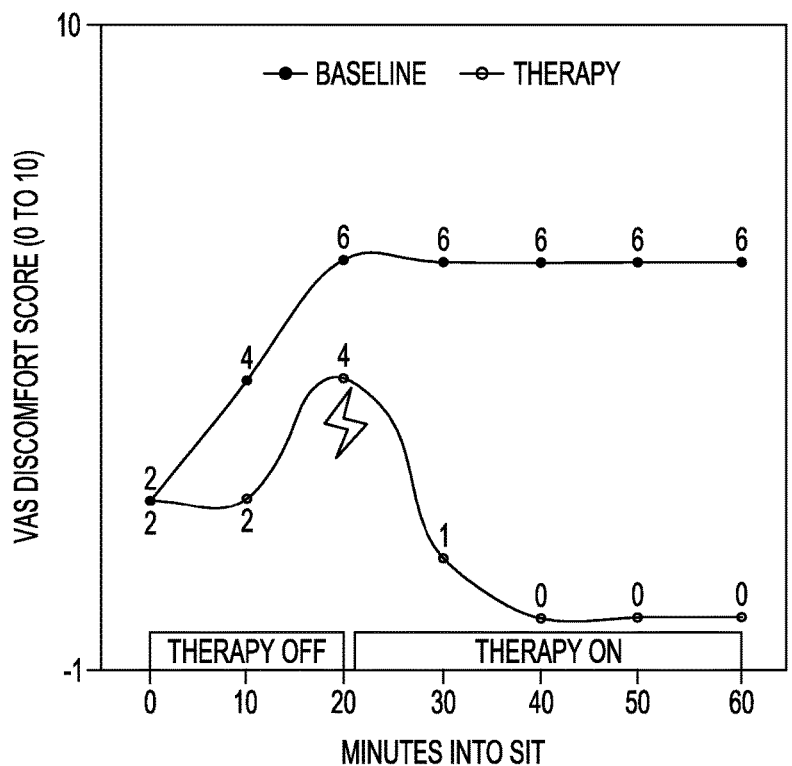
FIG. 3 shows an example of experimental Suggested Immobilization Test (SIT) data from a patient with severe RLS, who was on medications, "baseline" SIT data (without electrostimulation) and with "therapy" SIT data (with applied stimulation).

FIG. 3 shows an example of experimental SIT data from a patient with severe RLS, who was on medications (which medications were not withheld for the SIT study). The "baseline" SIT data (without any applied electrostimulation) shown in FIG. 3 shows increasing discomfort during the initial 20 minutes of the SIT study, followed by a steady level of discomfort at about 60% of the maximum discomfort level for the remainder of the SIT study. The "therapy" SIT data (with applied stimulation after the initial 20 minutes) was obtained from the same patient on the following night. The electrostimulation was transcutaneously applied to both the superficial peroneal nerves using a hydrogel-coated transcutaneous electrode, connected to a constant-current stimulator programmed to generate a waveform that stimulated the nerve with pulses that were 80-100 microseconds in duration, with an interval of 240-250 microseconds between them. The electrostimulation was turned on at minute 20. The patient reported a nearly instant relief from uncomfortable sensations in the feet when the electrostimulation therapy was turned on. The electrostimulation waveforms and amplitudes chosen were subsensory (such that the electrostimulation could not be sufficiently felt by the patient) and subthreshold (such that muscle activation did not occur in the patient as evidenced by any visual twitching or other sensations reported by patient), such that the patient could not identify whether therapy was turned on or off. Subsensory and subthreshold electrostimulation can be particularly beneficial in the present RLS application, such as to alleviate RLS symptoms while avoiding or minimizing the patient's perception of the electrostimulation being administered, such as to allow the patient to be able to fall asleep comfortably.

Figure 4:
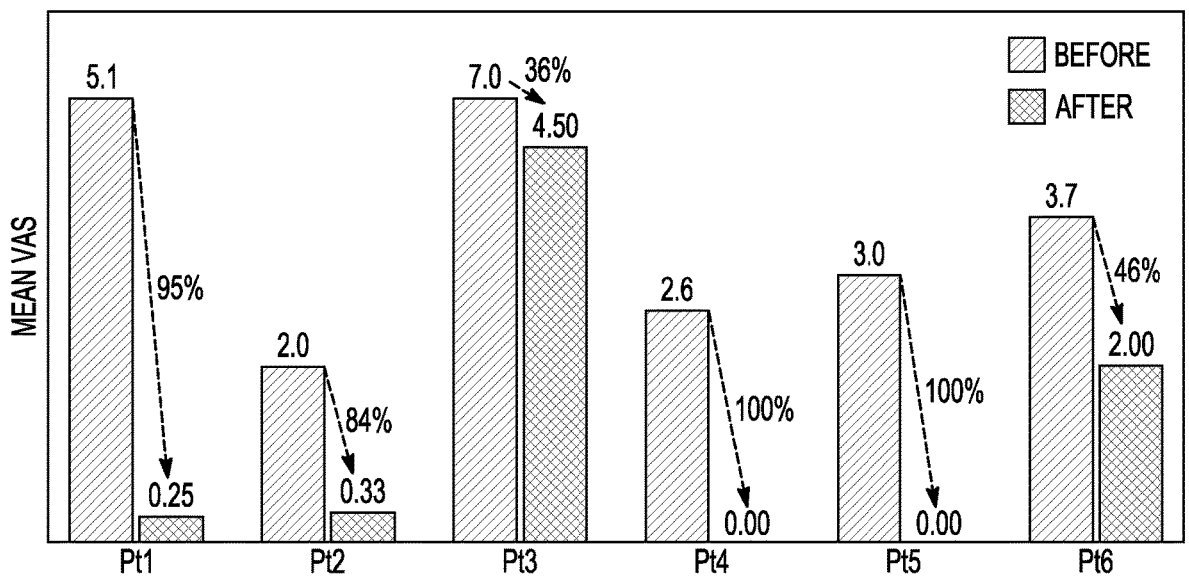
FIG. 4 shows an example summarizing SIT data results "before" and "after" electrostimulation of the superficial peroneal nerve target of six additional patients.

FIG. 4 shows an example summarizing SIT data results "before" and "after" electrostimulation of the superficial peroneal nerve target of six RLS patients that all met the criteria for "severe" RLS based on the International Restless Legs Syndrome Score (IRLSS) administered prior to enrollment. FIG. 4 demonstrates an example of a remarkable consistency in decrease of uncomfortable sensations associated with RLS in response to turning on electrostimulation of the superficial peroneal nerve.

Electrostimulation waveforms can be chosen specifically in frequency, shape, and amplitude such as to activate the large diameter A-Beta fibers that act to "gate" or block inputs from the smaller diameter A-Delta and C fibers that, in RLS patients, appear to be overactive and to transmit unpleasant sensations to the spinal cord, such as explained herein with respect to FIG. 2. In an example, a controlled-current electrostimulation waveform can be used, such as a charge-balanced square wave current waveform with current amplitudes delivered at a controlled current level that is between 5 milliamperes and 30 milliamperes or, such as was used for the patients represented in FIG. 4, at a controlled current level that is between 11 milliamperes and 25 milliamperes.

The present inventor has recognized, among other things, that high frequency ("HF", e.g., at a frequency between 500 Hz and 15,000 Hz, or even more particularly, between 4 kHz and 5 kHz) transcutaneous electrostimulation current waveforms can be—in this RLS application—preferred over low frequency ("LF", e.g., 150 Hz or below) transcutaneous electrical neurostimulation (TENS) waveforms. This is because, in an RLS therapy application, it is important to target these peripheral nerve fibers (such as the superficial peroneal nerve) with a subthreshold electrostimulation waveform that does not induce muscle contractions, as well as with a subsensory electrostimulation waveform that does not induce sharp sensations of electrostimulation (like most conventional LF sensory TENS waveforms, e.g., at 150 Hz or below), as this was observed to make RLS symptoms worse. Without being bound by theory, this could be attributed to patients with RLS having a strong hyper-sensitivity to any physical touch (tactile hyperalgesia) when RLS symptoms present and has been studied in the literature. Switching to a high-frequency (e.g., 4000 Hz-5000 Hz) subsensory electrostimulation waveform showed a marked improvement in RLS symptoms in some patients, such as shown in the example SIT data of FIG. 5.

Figure 5:
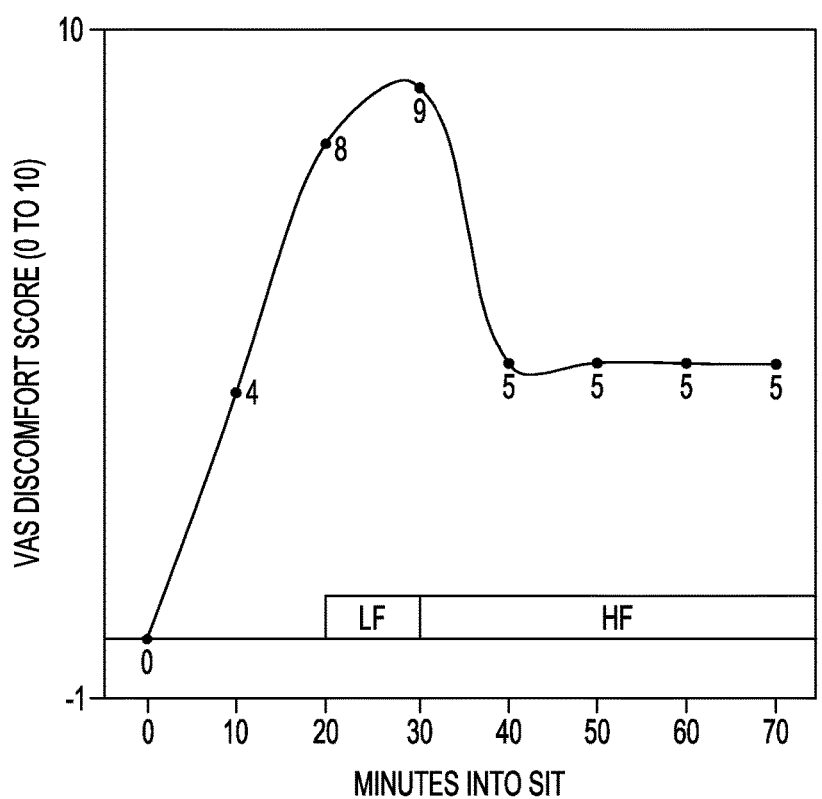
FIG. 5 shows an example of SIT data from a patient study in which a Burst sensory low-frequency (LF) TENS electrostimulation waveform was turned, then switching directly to a subsensory high-frequency (HF) electrostimulation waveform.

FIG. 5 shows an example of SIT data from a patient study in which a LF conventional (150 Hz) "Burst"-TENS electrostimulation waveform was turned on at minute 20, then switching directly to a HF (4000 Hz-5000 Hz) electrostimulation waveform at minute 30. During the initial 20 minutes of this SIT study (without any electrostimulation) patient discomfort climbed from 0 to 80% of the maximum possible score. With LF TENS electrostimulation, the patient's discomfort level actually increased to 90% of the maximum possible score. But after then turning on HF electrostimulation, the patient's discomfort level fell to 50% of the maximum possible score, indicating marked relief as compared to no electrostimulation or as compared to LF TENS electrostimulation.

Without being bound by theory, it is believed that this acute suppression of RLS symptoms using HF electrostimulation is because of the selective recruitment (e.g., activation via electrostimulation) of A-Beta fibers in the nerve targeted, which, in turn triggers release of GABA to block out the overactive A-Delta and C fibers, such as explained above with respect to FIG. 2. A sensed waveform indicating such selective activation may be obtained. This can include recording an evoked response from the electrostimulation stimulus (such as using a neural recording sense amplifier channel such as described herein), and, if needed, by re-adjusting one or more parameters of the electrostimulation stimulus, such as to obtain a desired pattern of activation, such as indicating selective recruitment of A-Beta fibers in the nerve targeted.

Figure 6:
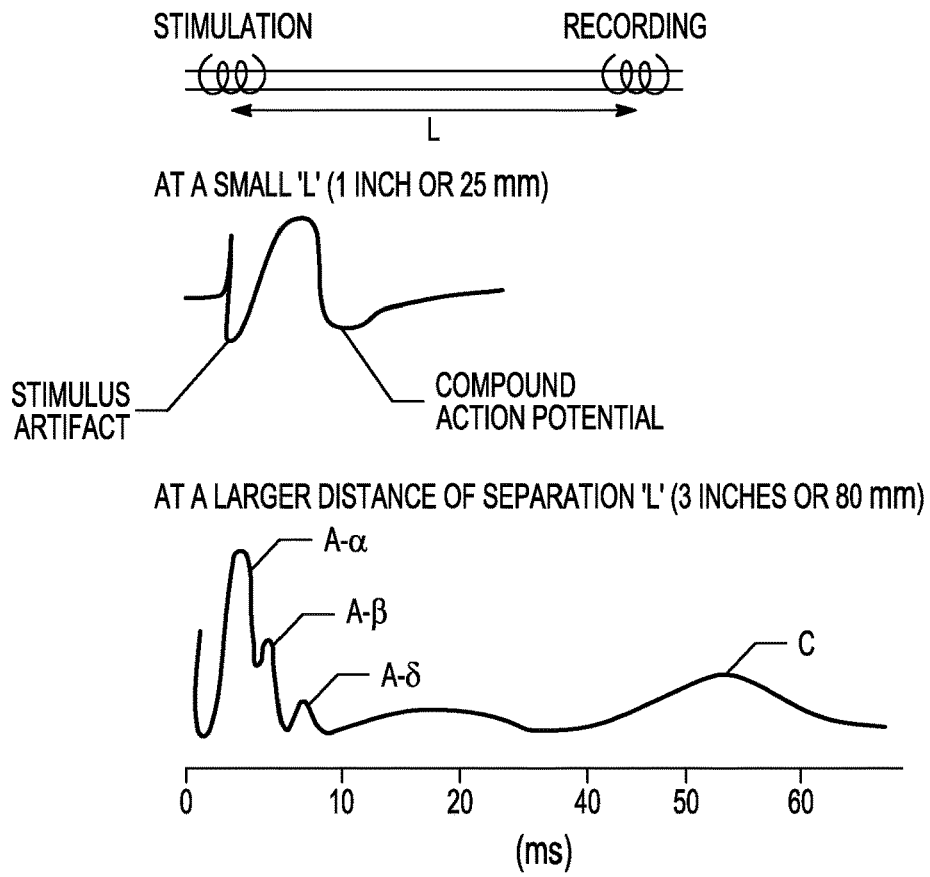
FIG. 6 illustrates conceptually an example of a resulting compound action potential (CAP) and the contribution of each nerve fiber sub-type, which can be sensed and recorded at a distance away from the applied electrostimulation.

FIG. 6 illustrates conceptually an example of a resulting compound action potential (CAP), and the contribution of each nerve fiber sub-type, that can be sensed and recorded along the length of the same nerve to which an electrostimulation is applied at a distance "L" away from the location of the applied electrostimulation. Sensing at two different distances "L" from the electrostimulation location are shown in the conceptual example of FIG. 6. At a larger distance of separation "L" conduction latency differences between the different nerve fiber sub-types can contribute to a unique morphology indicating which sub-type of nerve fiber has been selectively or preferentially recruited by a particular electrostimulation, such as relative to one or more other nerve fiber sub-types.

For example, in FIG. 6, at a smaller distance of "L" (e.g., ~1 inch or 25 mm), it can be difficult to observe each nerve-fiber component that contributes to the average CAP with the respective conduction velocities taken into account. However, if the sensing/recording electrode is moved farther downstream from the electrostimulation electrode along the length of the nerve, such as at a length "L" of ~80 mm or greater, the separate nerve-fiber components start to show up on the CAP as individual peaks. This is shown conceptually in FIG. 6 over a time period of about 60 ms after electrostimulation.

Based on a sensed/recorded CAP, it is possible to configure or optimize one or more electrical stimulation waveforms, such as to preferentially activate only a select sub-set of fibers, such as the A-Beta fibers. This method of detecting nerve fiber activation has been studied and reported in the technical literature. (See, e.g., Qing et al, IEEE Trans Neural Syst Rehabil Eng. 2015 November; 23(6):936-45.)

Figure 7:
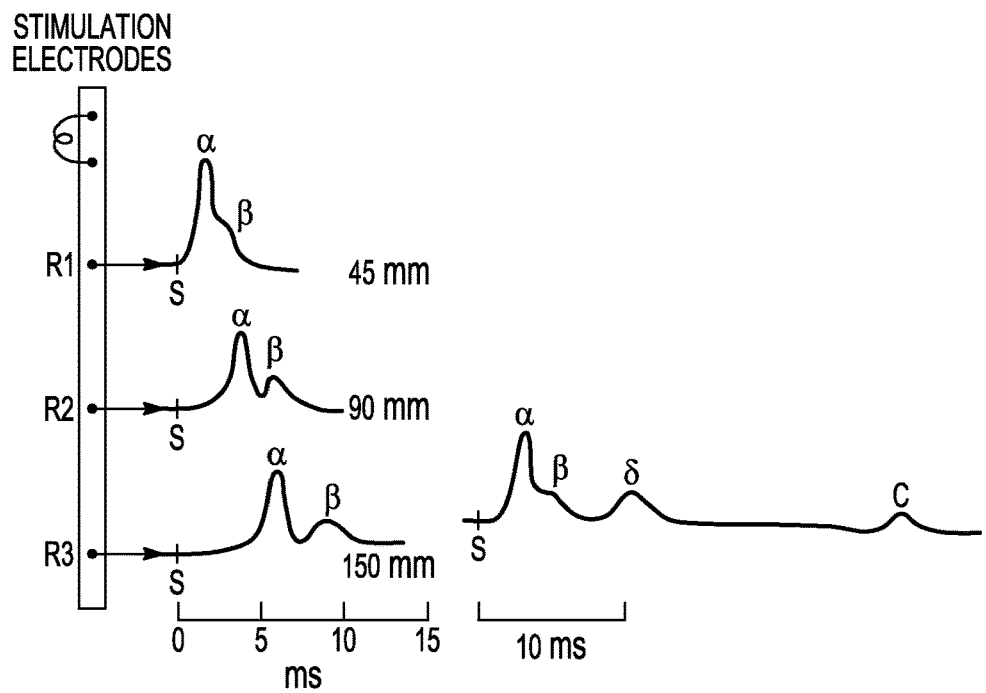
FIG. 7 illustrates a conceptual example of how each individual nerve fiber component may be detected.

FIG. 7 illustrates a conceptual example of how each individual nerve fiber component may be detected. This can include using a neural recording amplifier system that can be connected to a recording electrode that can be placed at one or more specified locations along the length of the nerve being stimulated upstream thereto.

Figure 8:
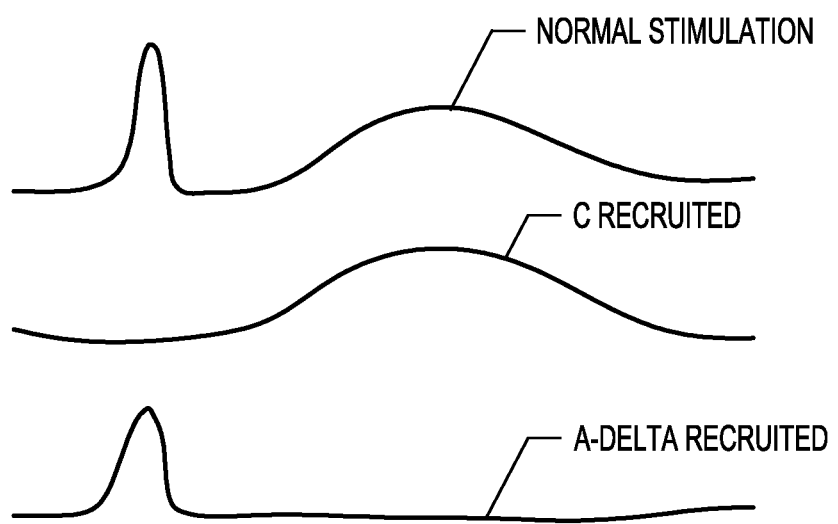
FIG. 8 illustrates a conceptual example of three different recording electrode waveforms, such as for comparing preferential and non-preferential recruitment or activation of a specific nerve fiber type, such as within a target nerve.

FIG. 8 illustrates a conceptual example of three different recording electrode waveforms. In the example of FIG. 8, the top waveform shows an example of an evoked response case in which no particular nerve fiber type is selectively or preferentially recruited by an applied electrostimulation. In FIG. 8, the middle waveform shows an example of an evoked response waveform in which the C fiber has been preferentially recruited by an applied electrostimulation, as indicated by the presence or dominance of a slower, lower frequency C fiber evoked potential over the absence or omission of a faster higher-frequency A-Delta evoked potential. The bottom waveform shows an example of an evoked response waveform in which the A-Delta fiber has been preferentially recruited by an applied electrostimulation, as indicated by the presence of dominance of a faster higher-frequency A-Delta evoked potential over the absence or omission of a slower, lower frequency C fiber evoked potential.

In an example, a CAP can be sensed, recorded, or measured. One or more parameters of the electrostimulation can be adjusted or optimized, such as to obtain a desired CAP response, such as one indicating preferential recruitment of one or more specific nerve fiber sub-types, such a selective recruitment of A-Delta fibers, such as explained herein. The system can include or use a set of transcutaneous electrodes to electrostimulate a designated target location of a target nerve, such as a targeted peripheral nerve (e.g., peroneal, sural, femoral, or a branch thereof, as an example) and a recording electrode can be located downstream of the targeted nerve or its targeted branch, such as to record a resulting evoked response signal.

In an illustrative, non-limiting example, first, a burst of electrical stimulation can be applied at the specified electrostimulation location, such as at a specified frequency (e.g., a frequency between 4 and 5 kiloHertz) such as for a specified duration (e.g., <10 milliseconds). Second, using hydrogel recording electrodes located at a specified distance from the electrostimulation electrode location, a resulting evoked CAP can be sensed using an electrically connected neural amplifier channel. Third, the electrostimulation intensity can be increased, such as until maximal evoked CAP amplitude is observed in the sensed or recorded signal. Fourth, one or more components A-Delta, A-Beta, or C fiber contributions from their characteristic individual peaks can be detected and averaged, such as over multiple bursts of electrostimulation. Fifth, one or more electrostimulation parameters can be adjusted, such as to modify the recorded CAP component amplitude peaks, such as to preferentially recruit one nerve fiber type subset over another, for a lower intensity of electrostimulation stimulus.

Similarly, to detect whether a particular electrostimulation waveform is preferentially recruiting one or more nerve fiber type subsets over another, the electrostimulation device under test (DUT) can be applied to a test impedance representative of a nerve target, such as to characterize the electrostimulation waveform. Then, the characterized electrostimulation waveform can be applied to a target nerve location, such as to observe the downstream evoked CAP and components attributable to one or more nerve-fiber types. Then, one or more parameters of the electrostimulation waveform can be varied, such as to determine whether a particularly emphasized component evoked in response to the previously-characterized electrostimulation waveform diminishes or disappears, such as relative to one or more other components of the evoked response waveform. For example, if one or more parameters of the electrostimulation parameters results in diminishing the A-Delta component observed in the evoked CAP relative to the C component of the evoked CAP, then it can be concluded that the characterized electrostimulation waveform was specifically tailored to preferentially recruit an A-Delta nerve fiber sub-type relative to a C fiber sub-type. Without being bound by theory, as explained herein, this can be desirable, such as to release GABA in the dorsal horn of the spinal cord, such as to help inhibit or suppress ectopic discharge activity from the targeted nerve, such as to alleviate one or more RLS symptoms.

Without being bound by theory, as explained herein such as with respect to FIG. 2, the activation of the larger diameter A-Beta fibers (or Type II fibers according to Lloyd's classification) has an inhibitory effect, such as by promoting the release of GABA that inhibits activity from the noxious stimuli carrying fibers (A-Delta and C fibers or Type III and Type IV, respectively). This was explained with respect to FIG. 2, and has been validated by the present inventor with clinical results obtained from patients with severe RLS symptoms.

In an example, the signaling cascade such as described with respect to FIG. 2 can be accomplished such as by activating one or more selected fibers (e.g., such as the A-Beta), such as in one or more peripheral nerves, such as a superficial peroneal or sural nerve (or branch thereof), which has demonstrated a near-instantaneous suppression of RLS symptoms. In an example, this can be established such as by using an electrostimulation with a carefully selected waveform, such as can range in frequency from 500 Hz to 10,000 Hz, in pulse width from 50 µS to 1 ms, and in current amplitude from 1 to 30 mA.

In a particular example, clinical data was obtained by switching between a LF waveform at 150 Hz and another, HF, waveform at 4,000 Hz with a pulse width of 50-100 µs. This allowed comparison of efficacy between LF and HF waveforms.

In another example, a 4000-5000 Hz randomly varying frequency waveform can be applied at the same time as a second waveform, which can be separated in frequency from the first, such as by 100-150 Hz, and can also be vary in approximately the same 4,000-5,000 Hz range (e.g., second frequency varying between 4100-5100 Hz).

Figure 9A:
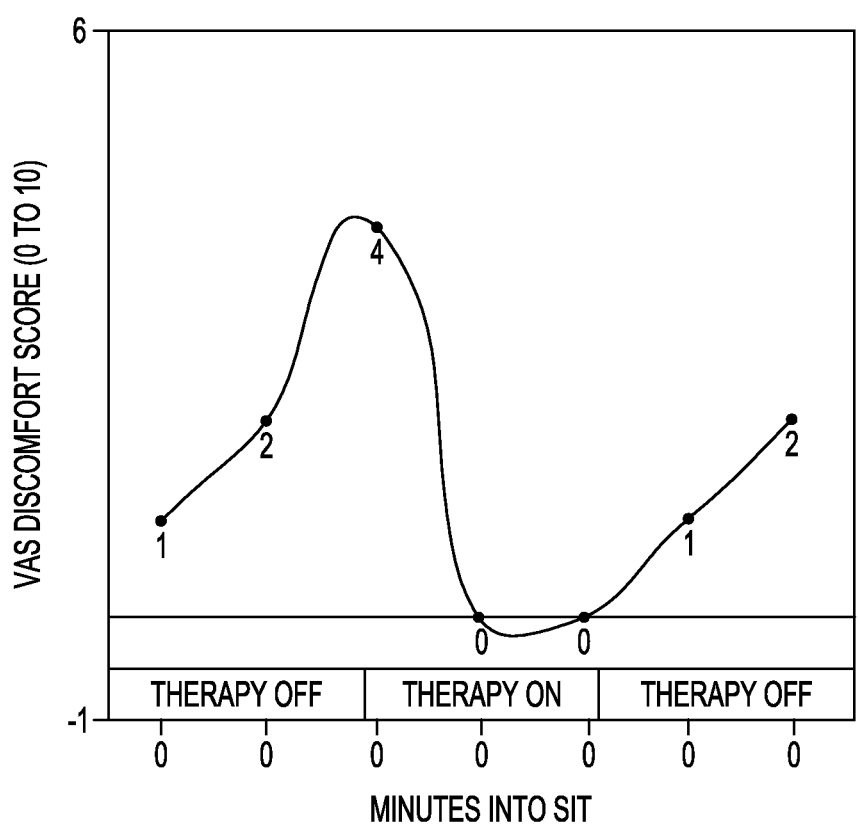
FIG. 9A shows an example of SIT data in which HF electrostimulation was turned on, then off, yielding suppression then resumption of RLS symptoms.

FIG. 9A shows an example of SIT data in which HF electrostimulation was turned on after an initial period of 20 minutes, providing near instantaneous suppression of RLS symptoms, and then turned off again at 40 minutes, triggering a resumption of RLS symptoms, further demonstrating acute efficacy of the HF electrostimulation, which is believed to provide the benefit of our proposed mechanism of action such as described above with respect to FIG. 2.

Figure 9B:
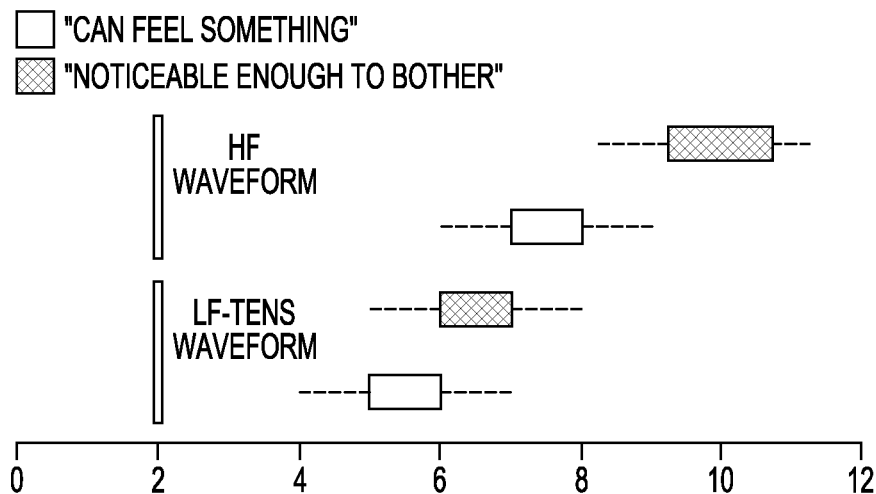
FIG. 9B shows an example of electrostimulation sensory comparative data for typical low frequency (LF) transcutaneous electrical neurostimulation waveforms as compared to a (HF) transcutaneous electrostimulation waveform according to the present techniques.

FIG. 9B shows an example of electrostimulation sensory comparative data for typical low frequency (LF) transcutaneous electrical neurostimulation waveforms as compared to a (HF) transcutaneous electrostimulation waveform according to the present techniques in N=5 normal subjects.

The parameters of the HF electrostimulation waveform can be carefully selected, such as to ensure maximal target nerve fiber activation for the least possible sensory perception threshold reported by patients. As shown in FIG. 9B, in randomized, blinded experimental tests performed on N=5 healthy controls, the HF electrostimulation waveform was applied at a frequency that was selected to be between 4000 and 5000 Hz—which was consistently able to deliver higher amounts of electrical current to the tissue before any sensory perception was reported by the patient, as compared to a typical LF TENS waveform at 150 Hz or below. Similar differences are also seen in thresholds at which patients reported discomfort, as shown in FIG. 9B.

Figure 9C:
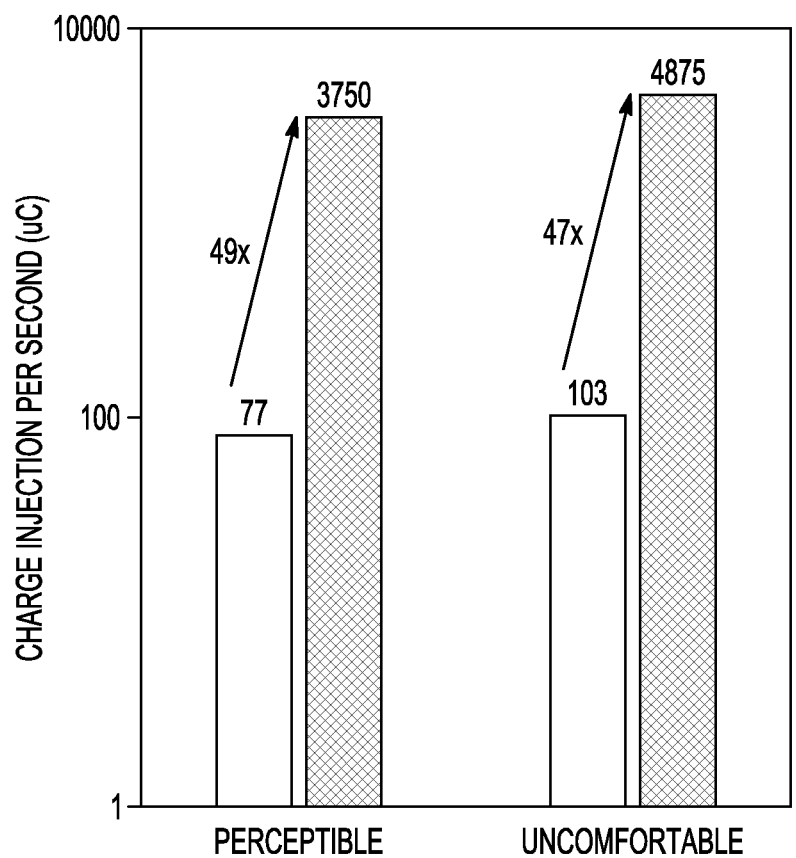
FIG. 9C shows calculated charge injection comparing the present HF waveforms with typical LF TENs waveforms.

FIG. 9C shows, according to calculations based on waveform shape and pulse widths, the HF waveforms (e.g., between 4000 and 5000 Hz) of the present techniques are able to inject 47 to 49 times more charge into the target tissue than conventional LF TENS (e.g., at 150 Hz or below) before the electrostimulation becomes perceptible, or before the electrostimulation becomes uncomfortable.

Figure 9D:
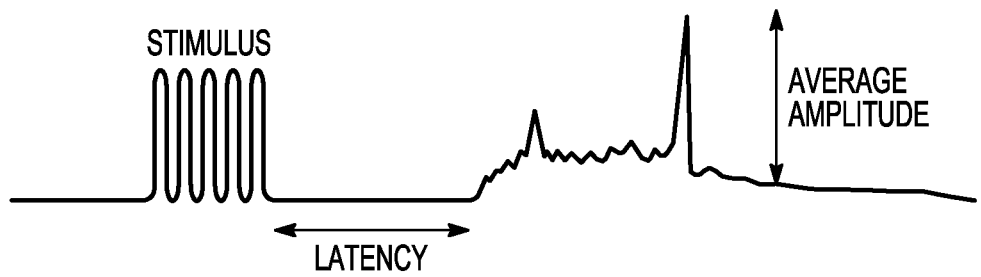
FIG. 9D shows a conceptualized (not real data) example of such a Flexion Reflex (Fr) response to a test electrostimulation stimulus.
Figure 9E:
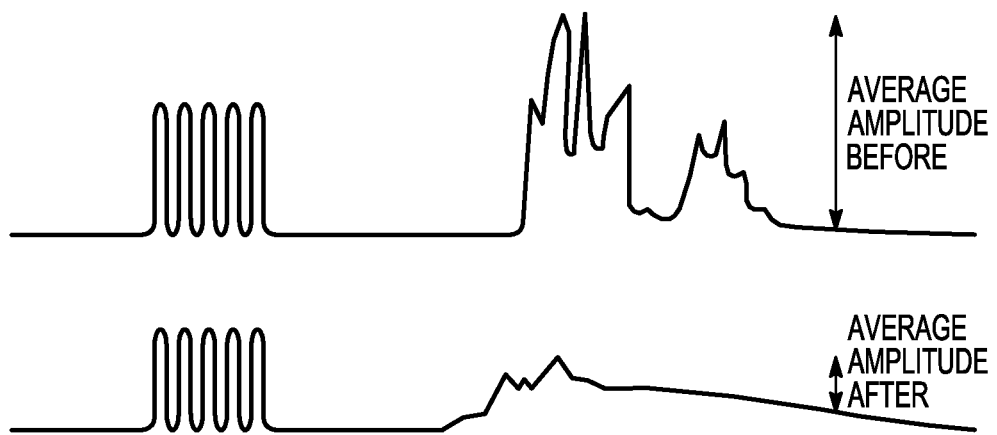
FIG. 9E shows a conceptualized (not real data) example of such Flexion Reflex Response amplitude to a test electrostimulation stimulus in the presence of a HF electrostimulation applied at a peripheral nerve, indicating a result of the inhibitory cascade of neural activation described in FIG. 2.

FIGS. 9D and 9E illustrate an example of using a Flexion Reflex response (Fr) to electrostimulation technique (e.g., that can be used additionally or alternatively to the CAP technique described herein) such as to establish or refine an electrostimulation waveform pattern, in patients receiving therapy. The flexion or flexor reflex (Fr) is a neurophysiological tool such as can be used to assess the efficacy of analgesic therapies, as stated by the European Federation of Neurological Societies (EFSN) guidelines. This Fr response can be elicited by electrical stimulation of a sensory nerve (e.g., sural nerve) and can be recorded from the flexor muscle in the ipsilateral limb (e.g., biceps femoris). The Fr includes an early response, the RII reflex (RIIr), and a late response, the RIII reflex (RIIIr). The RIIr is a non-nociceptive A-beta fiber mediated response, whereas the RIIIr is a high-threshold nociceptive A-delta fiber mediated reflex; the threshold of the RIIIr has been shown to correspond to the pain threshold and the size of the reflex to be related to the level of pain perception. The RIIIr is the more stable and reliably measured reflex and its amplitude is correlated to the intensity of pain perception, correlated to amount of nociceptive A-Delta activation.

In an example, the lower-limb flexion response may be elicited by delivering percutaneous electrical stimuli to the sural nerve through surface electrodes applied behind the right lateral malleolus and recording responses from the ipsilateral brevis head of the biceps femoris muscle. The stimulus can include a train of 5 electrical pulses (e.g., 1 to 5 milliseconds in duration, at a frequency that is between 100 and 250 Hz) and can be delivered randomly or pseudo-randomly such as at an interval that is between 5 and 20 seconds. FIG. 9D shows a conceptualized (not real data) example of such a Flexion Reflex (Fr) response to a test electrostimulation stimulus. The amount of stimulus current required to produce a reliable RIIIr waveform can be logged as the sensory threshold, and the electrostimulation can then be adjusted to be sub-sensory, such that it is beneath the sensory threshold of the patient and is not felt by the patient.

When the HF electrostimulation waveform is applied at a peripheral nerve (e.g., superficial peroneal nerve), a decrease in the amplitude of the flexion reflex response (RIIIr component) may be observed, indicating a result of the inhibitory cascade of neural activation described in FIG. 2, with a conceptual (not real data) example illustrating how this can be measured shown in FIG. 9E.

Figure 10:
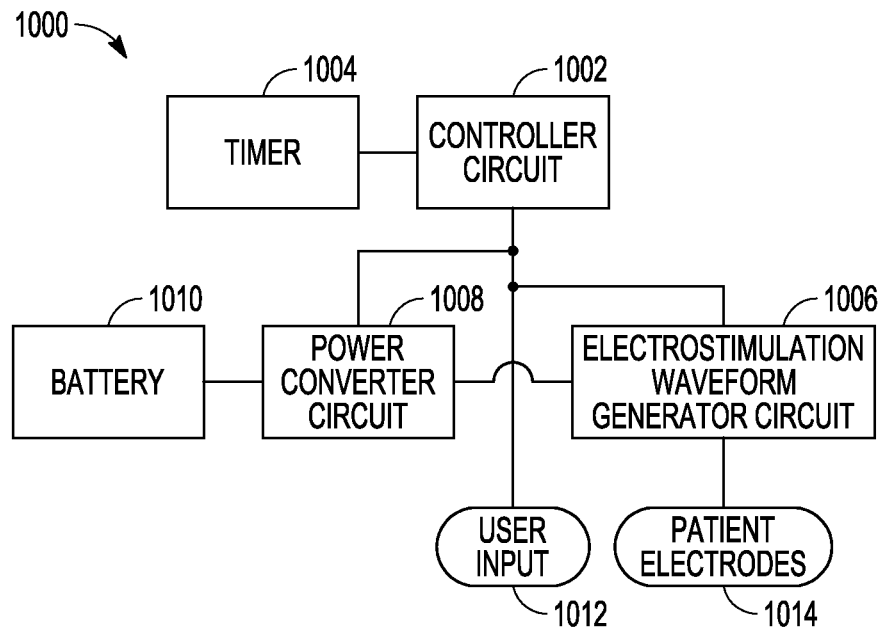
FIG. 10 shows an example of an open-loop RLS electrostimulation treatment system.

In FIG. 10, the RLS treatment system 1000 can include a controller circuit 1002, a battery 1010, a power converter circuit 1008, an electrostimulation waveform generator circuit 1006, a user input device 102, and patient electrodes 1014. In an example, the patient electrodes can include external electrodes, such as can be located on an adhesive skin-patch, such as for transcutaneous application of electrostimulation energy. In an example, the patient electrodes can include an implantable electrode, such as a nerve cuff that can be implanted such as to encircle a targeted nerve (e.g., a sural nerve) at a targeted location to position electrodes at the desired location. Implantable electronics can be included on the nerve cuff, such as to control delivery of the electrostimulation. The implantable electronics can be powered all or in part by RF or inductively-coupled energy that can be wirelessly coupled from an external transcutaneous electrical transmission (TET) source to an energy-receiving device on the implantable electronics.

The controller circuit 1002 can include a microprocessor, microcontroller, programmable logic circuit, or the like, such as can be powered by the battery 1010 or other power source. The battery can be coupled to a power converter circuit 1008, such as can include one or more of a buck power converter circuit, a boost power converter circuit, a buck-boost power converter circuit, or other inductive or capacitive or other circuit for converting the battery voltage and current to a desired output voltage and current such as for delivering electrostimulation to the subject via the patient electrodes 1014. An electrostimulation waveform generator circuit 1006 can receive a converted power signal from the power converter circuit 1008, and can generate a suitable electrostimulation waveform, such as a HF electrostimulation waveform such as described herein. For example, the electrostimulation waveform generator can be configured by the controller circuit 1002 to generate a HF electrostimulation controlled-current waveform such as having a frequency within a range of 4 kHz to 5 KHz and a current amplitude that can be controlled by the controller circuit 1002 such as set to a desired level such as within a range of 5 milliamperes to 30 milliamperes (e.g., at a level of 5 mA, 10 mA, 15 mA, 20 mA, 25 mA, or 30 mA, or finer resolution if desired).

In the example of FIG. 10 and the open-loop RLS treatment system 1000, a timer circuit 1004 can be included in or coupled to the controller circuit 1002, such as to control a duration for which the RLS electrostimulation treatment is applied after being turned on, such as by using a switch or other user input 1012 device. After the "on" duration established by the timer expires, the RLS electrostimulation treatment can be automatically turned off, thereby saving power extracted from the battery 1010. In an example, the timer duration can be an expected duration for the patient to fall asleep with the aid and assistance of the RLS electrostimulation treatment, such as at a programmable or other specified treatment duration value (e.g., 10 minutes, 15 minutes, 20 minutes, 25 minutes, 30 minutes, 45 minutes, 50 minutes, 55 minutes, 1 hour, or the like). In an example, the therapy can be ramped down upon expiration of the timer, rather than being abruptly turned off. The rampdown period can be specified, such as at a specified percentage of the treatment duration (e.g., 10%, 20%, 30%, 40%, 50%, or the like). The timer circuit 1004 can include a clock circuit, such that a time-of-day can be used to trigger a electrostimulation treatment session, such as of an electrostimulation treatment duration value as can be timed by the timer circuit 1004, such as described above.

Figure 11A:
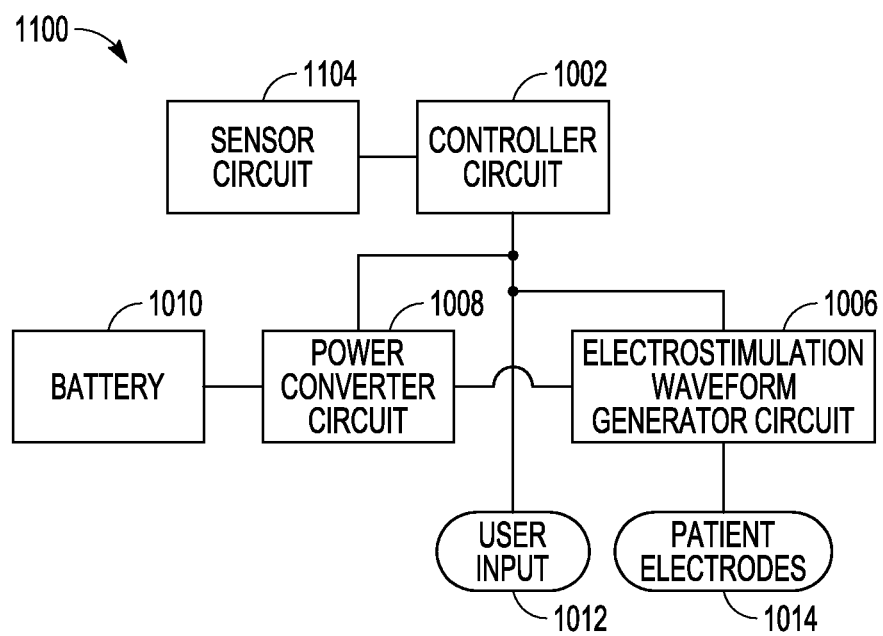
FIG. 11A shows an example of a closed-loop RLS electrostimulation treatment system.

FIG. 11A shows an example of a closed-loop RLS electrostimulation treatment system 1100, which is similar to the open-loop RLS electrostimulation treatment system shown in and described with respect to FIG. 10, but in which the timer 1004 can be replaced or augmented by a sensor circuit 1104. The sensor circuit 1104 can be used to sense a physiological or other similar parameter of the patient, and to control therapy using information about the parameter sensed by the sensor circuit 1104.

For example, such as where the RLS electrostimulation treatment system 1100 is worn on the patient's foot or lower limb, the sensor circuit 1104 can include an accelerometer or other motion sensor, such as can be configured to sense a leg motion of the patient. Information about the sensed leg motion can be used by the controller circuit 1002 to control a parameter of the electrostimulation. For example, electrostimulation can be turned on when a threshold number of symptomatic RLS leg twitches or motions have been sensed within a specified first sensing duration (e.g., within a duration that can be specified at 1 minute, 2 minutes, 5 minutes, or the like). This can be useful, for example, in a PLMD patient who can experience leg twitches or motions while sleeping, such as to automatically turn on (or increase) therapy to help mitigate symptoms to help the patient stay asleep. In an example, electrostimulation can be turned off (or can be ramped down or ramped off) when no RLS leg twitches or motions have been sensed within a second sensing duration (e.g., within a duration that can be specified at 1 minute, 2 minutes, 5 minutes, or the like). In an example, an electrostimulation amplitude can be increased when RLS twitches or motions have been sensed within a specified third sensing duration during which RLS electrostimulation therapy was being provided (e.g., persist beyond a duration that can be specified at 5 minutes, 10 minutes, or the like).

In an example, the sensor circuit 1104 can include a heart rate variability (HRV)-based or other sleep sensor, such as can be configured to sense whether the patient has fallen asleep, after which electrostimulation can be turned off (or can be ramped down or ramped off), or to detect a sleep state, and adjust an electrostimulation parameter based on the sleep state of the patient. The sleep sensor can be included and used together with the accelerometer, such as to detect leg twitches or motions while the subject is asleep, and automatically turn on (or increase) electrostimulation therapy in response. This can be useful for a PLMD patient who can experience leg twitches or motions while sleeping, such as to automatically turn on (or increase) therapy to help mitigate symptoms to help the patient stay asleep.

Figure 11B:
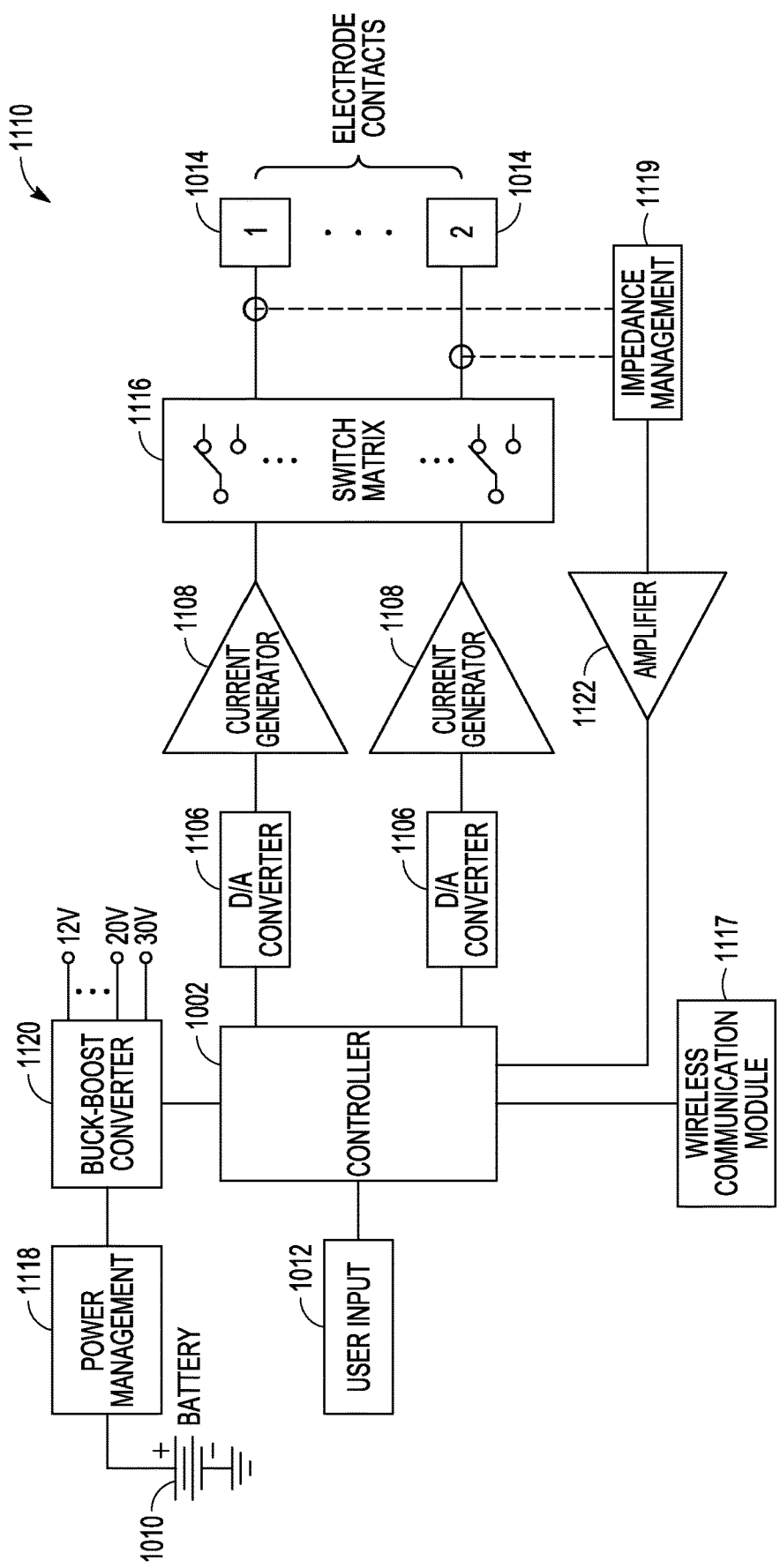
FIG. 11B shows an example of a block diagram of portions of an RLS electrostimulation system, such as can be configured to produce a controlled-current waveform, such as including when a variable load impedance is present.

FIG. 11B shows an example of a block diagram of portions of an RLS electrostimulation system 1110, such as can be configured to produce a controlled-current waveform (e.g., specified constant current amplitude AC electrostimulations) across a varying impedance present at an interface between the electrostimulation electrodes 1014 and the skin or other tissue of the patient contacted by such electrostimulation electrodes 1014.

In FIG. 11B, a power management circuit 1118 can be electrically connected or otherwise (e.g., wirelessly) interfaced to a power source, such as one or more rechargeable or other batteries 1110. The power management circuit 1118 can monitor a battery usability indication, such as can provide information about the amount of charge or other indicator of usable life remaining in the battery 1110. The power management circuit 1118 can provide an alert or can trigger automatic recharging (e.g., wirelessly or otherwise) of one or more of the batteries 1110, such as when depleted below a programmable, specifiable, or other threshold value.

The battery 1110 can be electrically connected or otherwise interfaced (e.g., through the power management circuit 1118) to a buck-boost power converter circuit 1120, such as can generate a programmable output DC voltage (e.g., 12V, 20V, 30V, or other specified DC output voltage. The DC output voltage needed can be determined by the controller circuit 1002, such as based on a sensed load impedance, which can vary, such as due to a varying electrode-tissue interface impedance. The load impedance can be measured using impedance sensing circuitry 1119. The impedance sensing circuitry 1119 can include one or more current sensing resistors, such as can sense a current at the electrodes. The current sensed by the current sensing resistors can be converted by the current sensing resistors into a voltage signal. The resulting voltage signal can be received at one or more inputs of an amplifier 1122, and can be buffered or amplified by the voltage amplifier 1122. The resulting buffered or amplified voltage signal can be digitized, such as by an analog-to-digital converter (ADC) circuit, such as can be included in or coupled to the controller circuit 1002.

The controller 1002 can use the sensed load impedance, which may be used by the controller 1002 in combination with other information, such as to determine the magnitude of the DC output voltage of the buck-boost converter 1120 needed to generate the desired electrostimulations, such as to conserve battery power while providing or maximizing therapeutic efficacy of the electrostimulations. The controller 1002 can establish one or more patterns of the desired electrostimulation, such as by using one or more stored electrostimulation waveform parameters that can be generated by the controller 1002. The controller 1002 can use the one or more stored electrostimulation parameters, such as to generate one or more analog electrostimulation control voltage waveforms, such as using a digital-to-analog (D/A) converter 1106. The resulting one or more generated analog electrostimulation control voltage waveforms can be converted to a proportionate, controlled, load-independent current, such as can include using one or more operational amplifier based current pumps 1108. The resulting controlled-current electrostimulation signals can be routed to a desired corresponding electrode 1014. Such routing can include using a multiplexer or switch matrix 1116. In an example, the switch matric 1116 can include one or more single-pole double-thrown (SPDT) switches, such as shown in the example of FIG. 11B, such as can be operated and controlled by the controller 1002, such as to dictate electrostimulation polarity, direction of electrostimulation field generated, to charge-balance or otherwise adjust or optimize the electrostimulation waveform, such as by selectively interfacing the controlled-current electrostimulation signal with the tissue at one or more target locations, such as using the electrode contacts 1014.

In an example, the controller 1002 can be interfaced with bidirectional or other wireless communication circuitry 1017, such as can include a transceiver circuit that can follow a protocol, such as Wi-Fi or Bluetooth, such as to communicate with or exchange information with a local external unit or with a remote server. A user-input module 1012 can also be configured to interface with the controller 1002, such as can include one or more aids to interact with the patient, with a caregiver, or with another user, for example, such as one or more push buttons or LED lights, such as to communicate information, to provide one or more status updates, or to turn on or off the RLS electrostimulation system 1110 or one or more components thereof.

One or more portions of the example shown in FIG. 11B can be combined with one or more portions of the example shown in FIG. 11A or with one or more portions of the example shown in FIG. 10, or with one or more portions of one or more other examples such as shown or described herein.

Figure 11C:
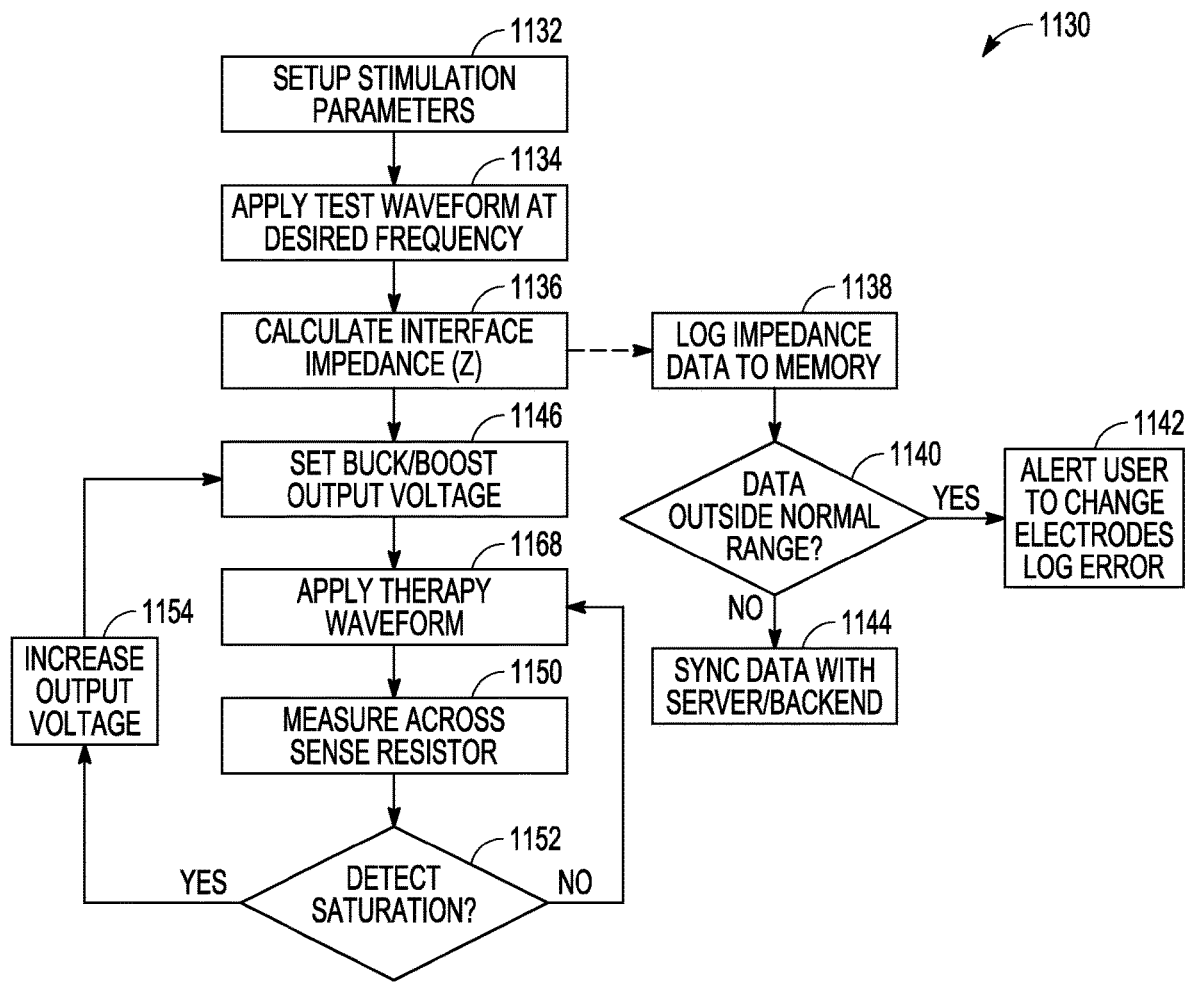
FIG. 11C is a flow chart showing generally an example of portions of a operating method, such as can be performed using the RLS electrostimulation system.

FIG. 11C is a flow chart showing generally an example of portions of a method 1130, such as can be performed using the RLS electrostimulation system 1130. At 1132, one or more electrostimulation parameters can be set up, such as by programming such information into memory storage in or coupled to the controller circuit 1002. Examples of such electrostimulation parameters can include one or more of amplitude, frequency, pulsewidth, duty cycle, pulse repetition frequency, or the like. At 1134, a test electrostimulation waveform can be delivered to the subject, such as via the electrodes 1014. At 1136, a load impedance or a component thereof, such as electrode-skin interface impedance can be calculated, such as by the controller circuit 1002, such as using a sensed impedance signal that can be measured using the impedance measurement circuit 1119, which can be buffered or amplified by the amplifier circuit 1122. By issuing a known voltage amplitude signal and measuring a response current signal (or vice-versa), such impedance can be determined. At 1138, the response signal data or calculated impedance data can be logged, such as by storing it to a memory location, such as within the controller circuit 1002. At 1140, it can be determined whether the measured electrode-skin interface impedance is outside a specified "normal" range, such as can include using one or more comparator circuits within the controller circuit 1002 or elsewhere, which can be provided one or more reference values for comparison for establishing the normal impedance range. If it is determined that the measured impedance data is outside the normal range, then at 1142, an alert can be generated to the patient or other user, such as to prompt replacement of the electrodes 1014, and an error condition can be logged in the controller circuit 1117, or communicated to a local or remote interface device or server system. Otherwise, at 1140, if it is determined that the measured impedance data is within the normal range, then at 1144, the measured impedance data can be logged in the controller circuit 1117, or communicated to a local or remote interface device or server system.

In FIG. 11C, after the skin-electrode interface impedance is calculated at 1136, this information can be used at 1146 to establish the DC output voltage to be provided by the buck/boost converter circuit 1120, such for use in generating the appropriate HF electrostimulation waveform, such as described above with respect to FIG. 11B. At 1148, the generated HF electrostimulation waveform can be applied to the patient via the electrodes 1014. At 1150, the generated HF electrostimulation waveform can be measured. This can include measuring the HF electrostimulation waveform current, such as by measuring the voltage across a sense resistor to provide a measurement indicative of the electrostimulation waveform current. At 1152, the measured value of the electrostimulation value can be compared to a saturation threshold value, such as can include using a comparator, such as can be included within the controller circuit 1102. If the result of the comparison indicates the presence of a saturation condition, then at 1154, the DC output voltage of the buck-boost converter circuit 1120 can be increased for subsequent application of the electrostimulation energy. Otherwise, the DC output voltage of the buck-boost converter can be maintained for subsequent application of the electrostimulation energy.

Figure 12:
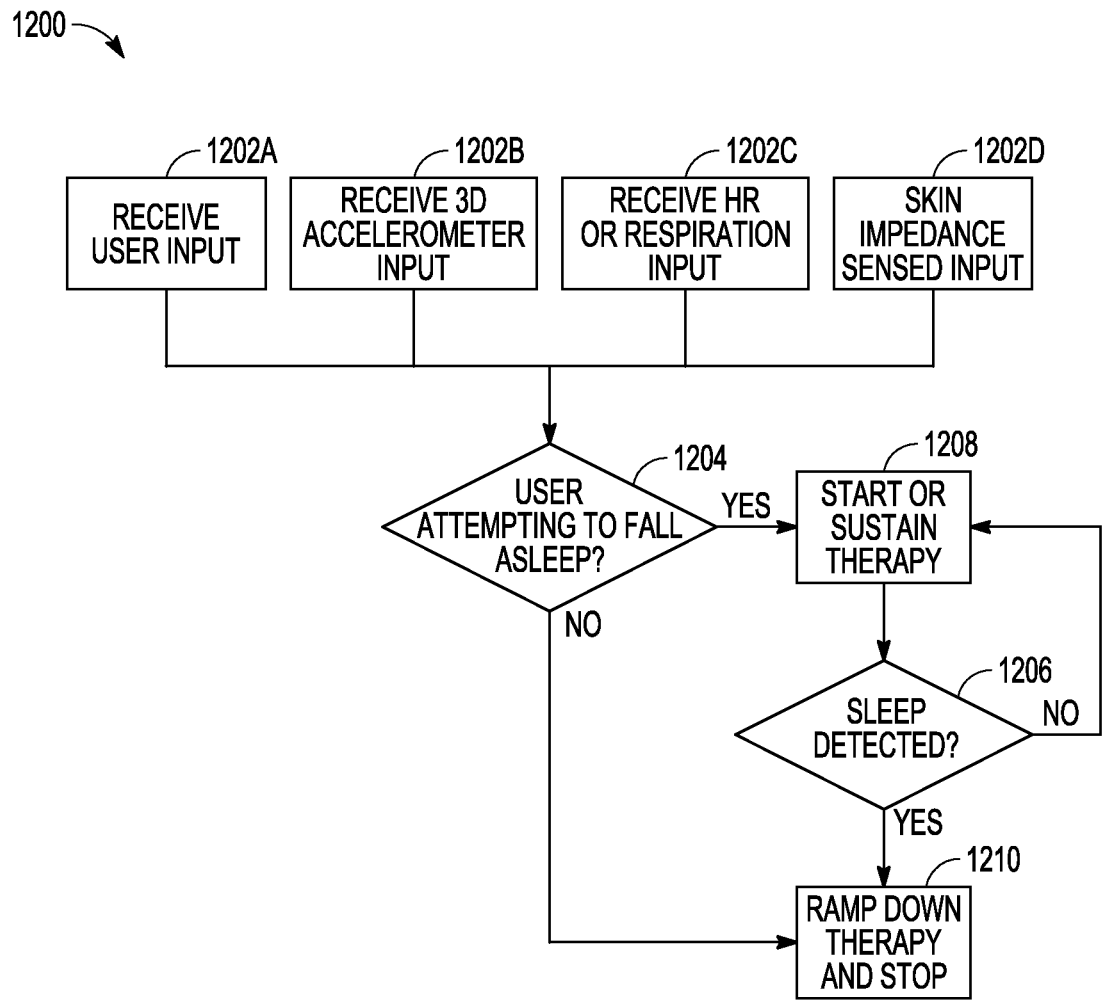
FIG. 12 shows an example of a technique for using one or more sensor circuits or the user input device, or both, such as for controlling RLS electrostimulation therapy delivery.

FIG. 12 shows an example of a technique 1200 for using one or more sensor circuits 1104 or the user inputs device 102, or both, such as for controlling RLS electrostimulation therapy delivery, such as by the closed loop RLS electrostimulation therapy system 1100. At 1202, for controlling RLS therapy delivery, one or more of user input can be received (1202A), 3D accelerometer input can be received (1202B), a sensed heart rate (HR) or respiration input signal can be received (1202C), a sensed skin impedance input signal can be received (1202D), such as by the controller circuit 1002, such as for use in determining whether the patient is attempting to fall asleep at 1204, or whether onset of sleep has been detected at 1206.

For example, a user can actuate a switch or can provide other user input at 1202A, such as for signaling to the system 1100 that the patient is intending to fall asleep. Sleep detection can be performed by the controller circuit 1002, such as by using information from the 3D accelerometer at 1202B to determine a position of the patient (e.g., upright vs. recumbent) or of the patient's lower limb, or whether leg activity movement indicates RLS symptoms, such as leg twitches or motion, or is consistent with sleep. A heart rate can be sensed (e.g., via the patient electrodes 1014 or via separate electrodes that can be placed or located in contact with the patient), and a heart rate variability (HRV) parameter can be calculated by the controller circuit 1002 from the sensed heart rate signal. HRV can be used to detect sleep or to detect a particular state of sleep. A respiration (breathing) signal can be sensed (e.g., via the patient electrodes 1014 or via separate electrodes that can be placed or located in contact with the patient) such as by using an impedance sensor to detect respiration, which will modulate the detected impedance. Sleep state information can be extracted from the respiration signal, such as by signal processing such as can be performed by the controller circuit 1002. Sleep state information can also be obtained by interfacing with other sleep monitoring products that a patient may use, such as can communicate this information to the controller circuit 1002. A skin impedance sensor can be used to detect frequency-dependent impedances using the patient electrodes 1014 or other changes in skin impedance, such as can provide information about the subject's sleep state, such as by processing such information as can be performed by the controller circuit 1002.

An autonomic balance sensor or indicator can be used to detect a state of a balance between the subject's sympathetic and parasympathetic nervous systems. Such information can be used to adjust an electrostimulation parameter. This can include adjusting an electrostimulation level to provide a higher degree of electrostimulation corresponding to a higher level of sympathetic nervous system assertion relative to parasympathetic nervous system assertion.

A posture sensor can be used to detect a state of a patient's posture, which information can be used to adjust one or more electrostimulation parameters. For example, in a patient with RLS symptoms that are worse when the patient is trying to sleep upright (e.g., in a seat on an airplane) as opposed to when the patient is trying to sleep while lying down in a recumbent position, such posture information can be used to increase titration of electrostimulation therapy when the former case occurs, relative to when the latter case occurs.

At 1204, it can be determined whether the patient/user is attempting to fall asleep. For example, a user can actuate a switch or can provide other user input at 1202A, such as for signaling to the system 1100 that the patient is intending to fall asleep. In an example, a transition of the patient into a recumbent position can be used as an indication that the patient is attempting to fall asleep.

At 1204, if the patient/user is attempting to fall asleep, then at 1208, RLS electrostimulation therapy can be initiated or, if already ongoing, sustained. Otherwise, at 1204, if the patient/user is not attempting to fall asleep, then process flow can proceed to 1210, in which ongoing RLS electrostimulation therapy (if any) can be ramped down and stopped. At 1208, starting RLS therapy can include initiating therapy using an initial set of electrostimulation parameter values, such as can include, in an example, a stored set of electrostimulation parameters, such as can be selected based on previous efficacy in the patient. Such efficacy can be determined by user survey input ranking the efficacy, or by detecting a quantity of RLS symptoms (e.g., leg twitches or movements) over time after initiating an RLS electrostimulation therapy session. Electrostimulation parameter values can also be chosen based on the state of sleep (e.g., N1-N4, REM/NREM, or the like), such as can be detected by the controller circuit 1002 either using one of the on-board sensors 1104 or using a different sleep monitoring device that the patient may use, such as can communicate with the controller circuit 1002. As an example, the controller circuit 1002 can elect to choose electrostimulation parameter values that are optimized to have lower sensory perception when a light or early stage of sleep is detected such as to prevent any disruption of sleep in the patient.

At 1206, if after initiating electrostimulation therapy sleep is detected, then process flow can continue to 1210, such as to cease electrostimulation or to ramp down therapy electrostimulation energy toward then ceasing electrostimulation. This can help save power and avoid unnecessary therapy while the subject is asleep. Otherwise, at 1206, if after initiating electrostimulation therapy sleep is not detected, then process flow can return to 1208, such as to sustain electrostimulation therapy, such as until such time that sleep onset can be detected at 1206.

Figure 13:
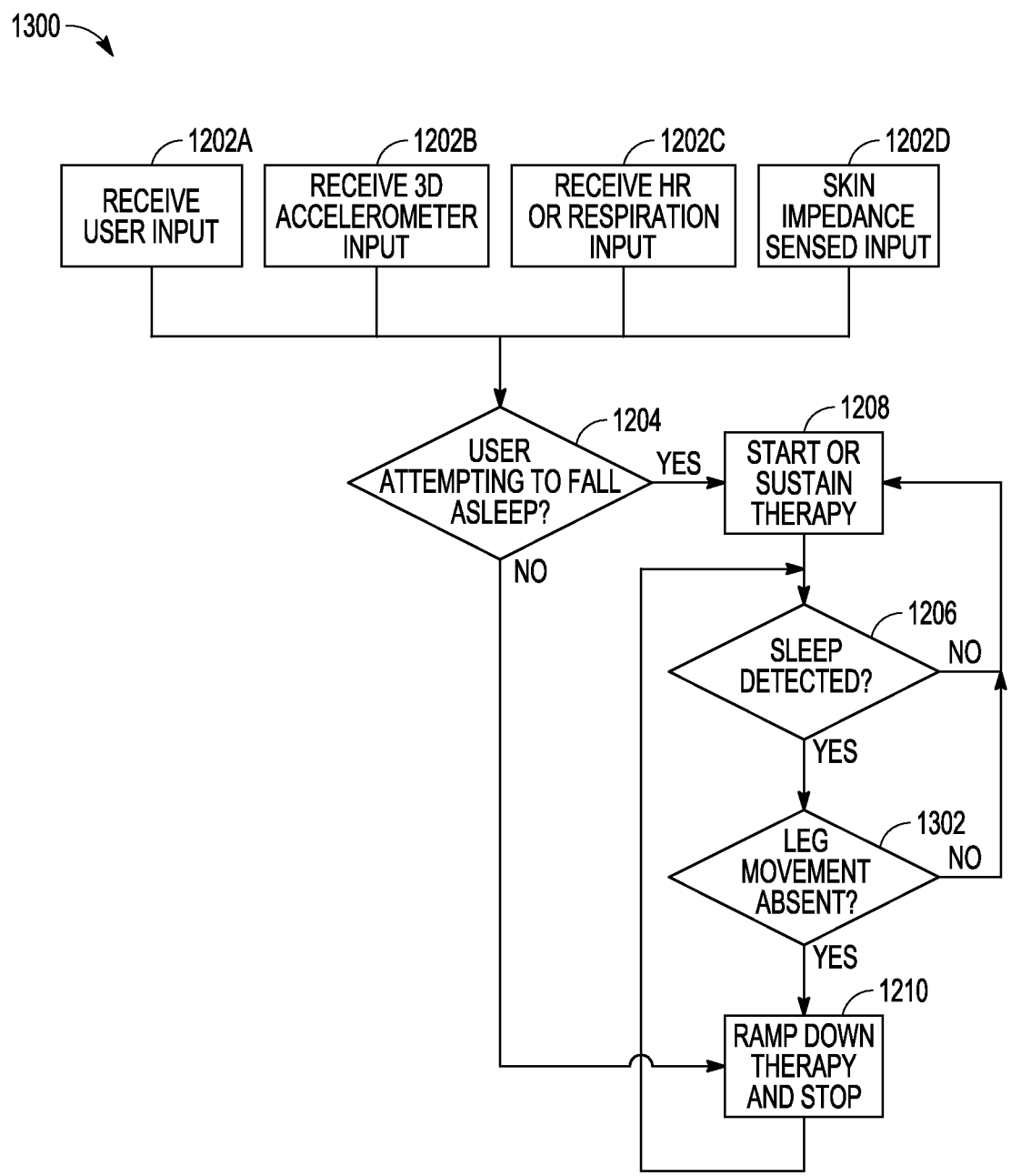
FIG. 13 shows an example of a technique, similar to the technique shown in and described with respect to FIG. 12, but modified to address episodes of leg twitching or motion occurring after the subject falls asleep, such as can occur in periodic limb movement disorder (PLMD) patients.

FIG. 13 shows an example of a technique 1300, similar to the technique 1200, shown in and described with respect to FIG. 12, but modified to address episodes of leg twitching or motion occurring after the subject falls asleep, such as can occur in PLMD patients. In the example of FIG. 13, the technique 1300 can proceed as described with respect to FIG. 12 until after sleep is detected at 1206.

At 1206, if sleep is detected, then monitoring can continue until a specified period of time has elapsed (e.g., 10 minutes, 15 minutes, or 20 minutes) with leg movement being absent, or being less than a specified threshold amount of leg movement during and over the specified period of time, after which process flow can proceed to 1210, to cease or to ramp down and cease electrostimulation therapy. However, since in a PLMD patient, episodes of leg twitching or movement can recur while the subject is sleeping, process flow can proceed from 1210 back to 1206, to continue to monitor the patient for sleep at 1206, and then for leg movement during sleep, at 1302. If such monitoring indicates that the patient has awoken, RLS electrostimulation therapy can be resumed at 1208. If such monitoring indicates that the patient has continued sleeping, but has experienced a sufficient degree of leg twitching or movement during such sleep, then electrostimulation therapy can be resumed at 1208. Otherwise, any ongoing electrostimulation can be ramped down and stopped at 1210, subject to further sleep monitoring at 1206 and further leg movement monitoring at 1302.

Figure 14:
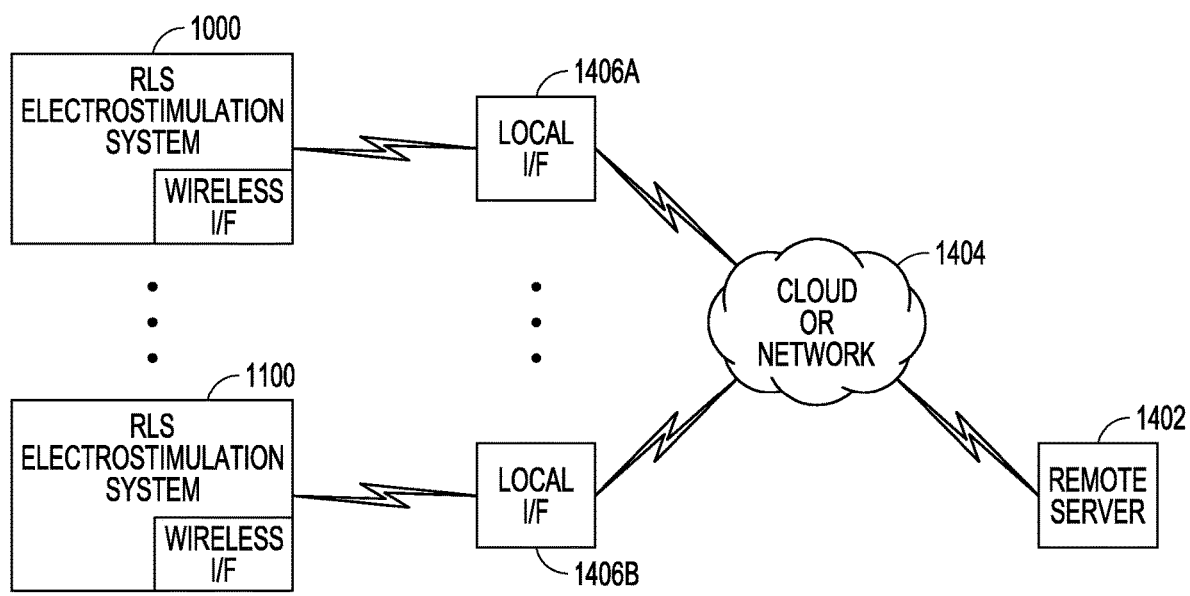
FIG. 14 shows an example in which one or more of the open-loop RLS electrostimulation systems or one or of the closed-loop RLS electrostimulation systems, or both, can be communicatively coupled to a remote server such as via a cloud or communication network.

FIG. 14 shows an example in which one or more of the open-loop RLS electrostimulation systems 1000 or one or of the closed-loop RLS electrostimulation systems 1100, or both, can be communicatively coupled to a remote server 1402 such as via a cloud or communication network 1404. This can include optionally using a repeater or other local interface device 1406, such as can establish a Bluetooth or other low-power wireless connection with a local RLS electrostimulation system 1000, 1100, for interfacing with the remote server 1402.

Remote server 1402 can be used for logging, processing, or analysis of data from the individual RLS electrostimulation system 1000, 1100 instances associated with respective patients. The remote server 1402 can include a library of patient data, such as can include waveform and efficacy data from previous episodes of various patients. The remote server 1402 can include a neural network, artificial intelligence, or machine learning system that can use efficacy data about waveforms used in various patients obtaining various results, such as for recommending a particular electrostimulation waveform or electrostimulation parameter to a particular patient, such as based on previous data from that patient or from a population of patients. Such recommendation can be based at least in part on a similarity of one or more characteristics between a target patient and patients in the patient population included in the library.

Figure 15:
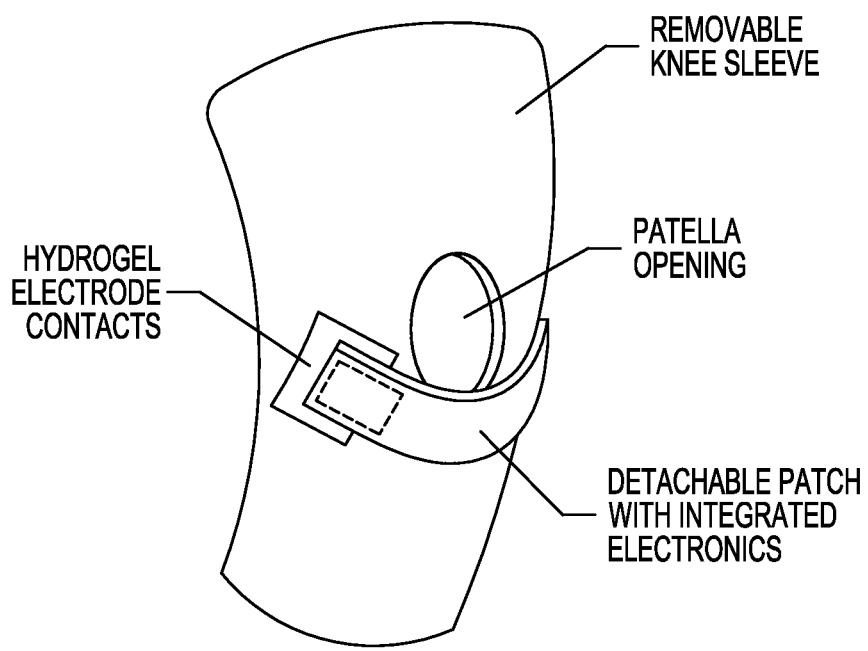
FIG. 15 includes an example of a stabilizer, such as to carry or hold all or portions of an RLS electrostimulation system in place.

FIG. 15 includes an example of a stabilizer, such as to carry or hold all or portions of an RLS electrostimulation system 1000, 1100 in place. In FIG. 15, the stabilizer can include a spandex or other elastic wearable and removable knee sleeve, such as can include an elastic patella opening formed therein, such as to allow the patient's patella to protrude therefrom. A disposable or other detachable adhesive patch can carry or hold integrated electronics of the RLS electrostimulation system 1000, 1100, and can also include integrated hydrogel or other electrodes, such as can contact the patient's skin through corresponding openings in the knee sleeve such as can correspond to one or more desired locations of the targeted nerve to which electrostimulation is to be delivered for RLS therapy. In this way, positioning relative to the target nerve location can easily be made, such as by using the patient's patella as a landmark with respect to which the sleeve is positioned, which, in turn, can serve to appropriately position the electrodes at the desired locations with respect to the corresponding target nerve locations.

Figure 16A:
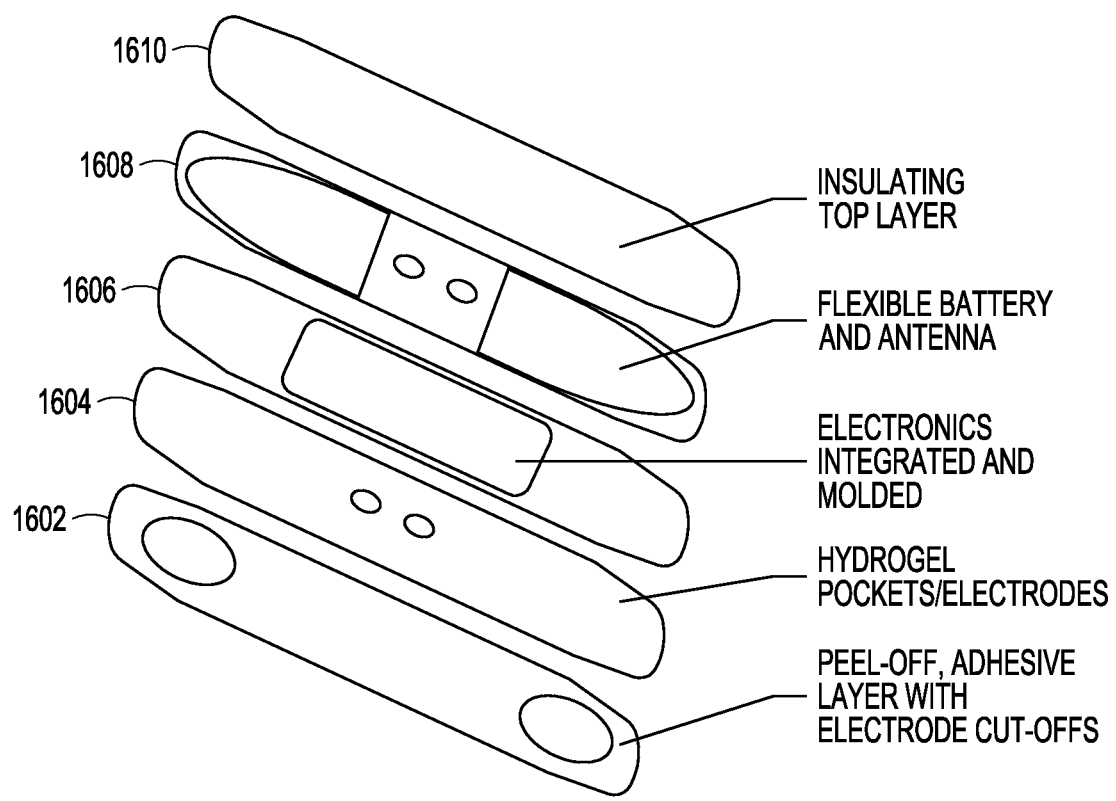
FIG. 16A shows a multilayer example of various layers of the disposable or other detachable patch, such as shown in FIG. 15 in use with the knee sleeve.

FIG. 16A shows a multilayer example of various layers of the disposable or other detachable patch 1600, such as shown in FIG. 15 in use with the knee sleeve. In this example, the most proximal (closest to the patient) layer 1602 can include a peel-off layer over an adhesive underlayer with electrode cutouts. The next most proximal layer 1604 can include hydrogel pockets or electrodes, such as can be similarly shaped and aligned with the cutouts in the layer 1602. The next most proximal layer 1606 can include or carry an electronics unit of the RLS electrostimulation system 1000, 1100, such as with conductive traces for providing electrical contact with and connection to the electrodes in the layer 1604 or to one or more other components. The next most proximal layer 1608 can include a flexible battery and antenna, such as with electrical connections to the underlying electronics unit that can be carried by the underlying layer 1606. The next most proximal layer 1610 can be the most distal layer, and can include an electrically insulating top layer, at least a periphery of which can be bonded to one or more of the underlying layers. In an example, the electronics unit can be detachable from the other components, such as using a clasp or locking mechanism, such as to permit re-use of the electronics unit together with disposability of the other components of the patch.

Figure 16B:
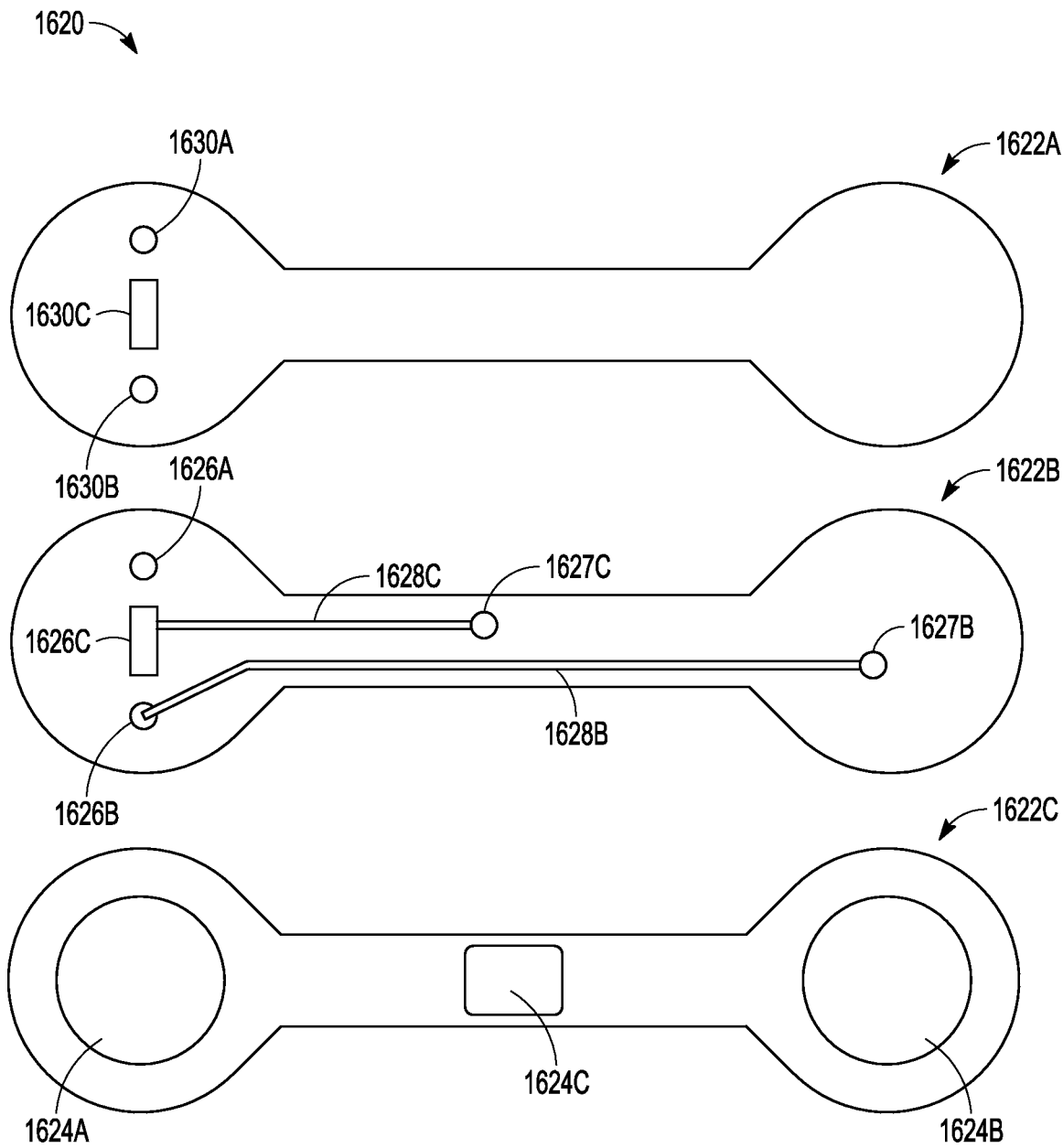
FIG. 16B shows an example of portions of a stabilizer, such as can include a multi-layer disposable or other detachable patch, such as can be separately attachable to an electronics unit.

FIG. 16B shows an example of portions of a stabilizer, such as can include a multi-layer disposable or other user-attachable and user-detachable patch 1620, such as can be separately attachable to a detachable (e.g., optionally re-usable) electronics unit 1640 (FIG. 15C), and such as can optionally be used with the knee sleeve shown in FIG. 15. The patch 1620 is shown as sized, shaped, or otherwise configured to be particularly suitable for placement to target a peroneal nerve or femoral nerve such as for delivering targeted electrostimulation thereto. The detachable patch 1620 can include a top layer 1622A, a middle layer 1622B, and a bottom layer, 1622C. These layers can be similarly shaped to each other, such that, when stacked, they can define circular, flared out, or other flared out ends or lobes. These ends can be interconnected by a rectangular or other strip of a desired length, such as to obtain a desired positioning of the electrodes. The electrodes can be placed at appropriately spaced-apart desired locations at the ends, or at an appropriate location on the interconnecting strip, such as for delivering the electrostimulations to a targeted nerve location (e.g., femoral nerve, peroneal never, sural nerve, or one or more branches thereof, or the like). Including a return electrode 1624C at an appropriate location in a middle portion of the interconnecting strip can provide a return electrode location that is close to the electrodes at the ends, which can target desired electrostimulation nerve target locations, but safely away from other nerves (e.g., in a peroneal nerve target placement), such as can help avoid undesired electrostimulation of such other nerves. In the bottom layer 1622C, electrodes 1624 can include hydrogel pockets that can be carried at selected locations of the bottom layer 1622C, such as at one or more desired locations at the ends of the bottom layer 162C2, or at one or more desired locations along the interconnecting strip of the bottom layer 1622C, such as for contacting underlying skin. The hydrogel carried in such hydrogel pockets associated with the electrodes 1624 can be electrically conductive. This can help provide low electrode-skin interface impedance for the electrodes 1624.

The middle layer 1622B can include vias 1626, 1627 and conductive traces 1628, such as for interconnecting the electrodes 1624 to respective metal or other electrically conductive contacts 1630 on the top layer 1622A, such as at one of its ends, or to one of the electrodes 1624 on the bottom layer 1622C. A detachable electronics unit 1640 (FIG. 16C) can be attached to the top layer 1622A, such as with respective contacts matching the locations of the contacts 1630. The contacts on the detachable electronics unit 1640 (FIG. 16C) can be magnetized, such as to provide a magnetic attraction force with the contacts 1630 on the top layer 1622A. This magnetic attraction force can hold the detachable electronics unit 1640 (FIG. 16C) in place with respect to the top layer 1622A, and can allow self-alignment of the detachable electronics unit 1640 (FIG. 16C) to the appropriate contacts of the top layer 1622A.

Figure 16C:
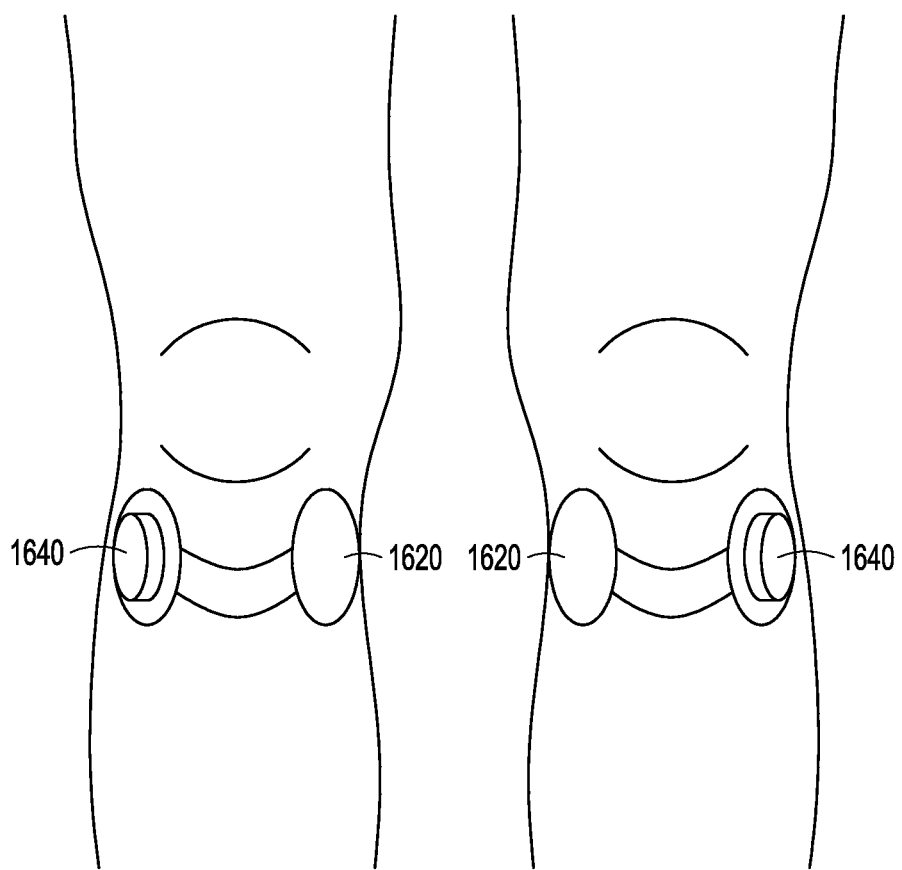
FIG. 16C shows an example of placement of the detachable adhesive patch of FIG. 16B, such as at a peroneal nerve target location, just below the knee on an anterior portion of the lower limb, with a detachable electronics unit.

FIG. 16C shows an example of placement of the detachable adhesive patch 1620 of FIG. 16B, such as at a peroneal nerve target location, just below the knee on an anterior portion of the lower limb, with the detachable electronics unit 1640 magnetically or otherwise attached to the detachable adhesive patch 1620.

Figure 16D:
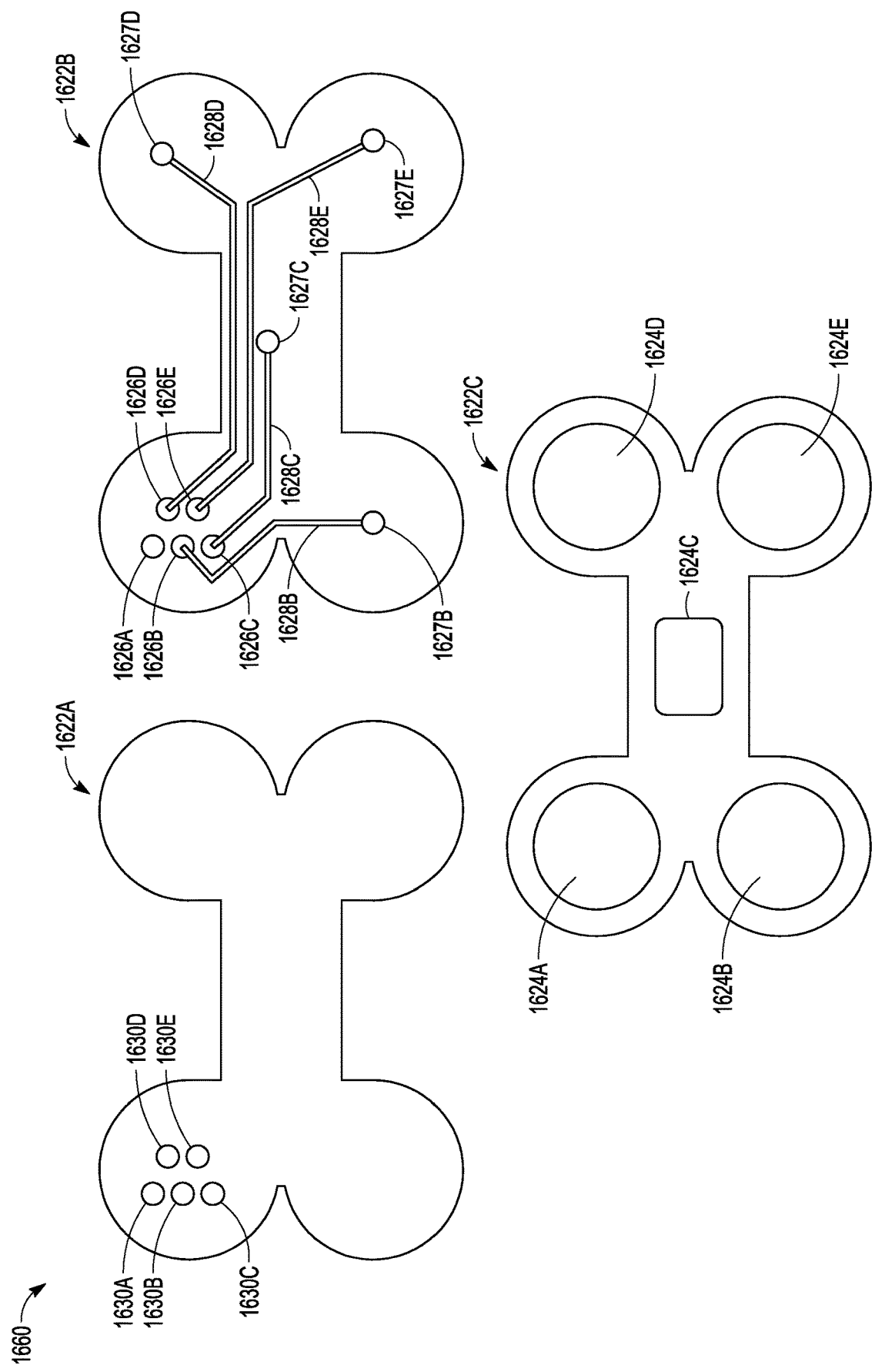
FIG. 16D shows an example of portions of a stabilizer, such as can include a multi-layer disposable or other detachable patch, similar to the patch shown in FIG. 16B, but shown with bilateral lobes, such as can provide additional hydrogel electrode locations.

FIG. 16D shows an example of portions of a stabilizer, such as can include a multi-layer disposable or other detachable patch 1660, similar to the patch 1620 shown in FIG. 16B, but with the patch 1660 shown including 5 electrodes, as compared to the 3 electrodes of the patch 1620 shown in FIG. 16B. In the example of FIG. 16D, the ends can include flared circular or other lobes, such as can extend laterally in opposing directions from each end of the patch 1660. The detachable electronics unit 1640 can be attached over one of these lobes, in magnetic self-alignment or otherwise, such as to provide aligned contact between a similar arrangement of contacts on the detachable electronics unit 1640 as the arrangement of contacts 1630 shown in FIG. 16C.

Figure 16E:
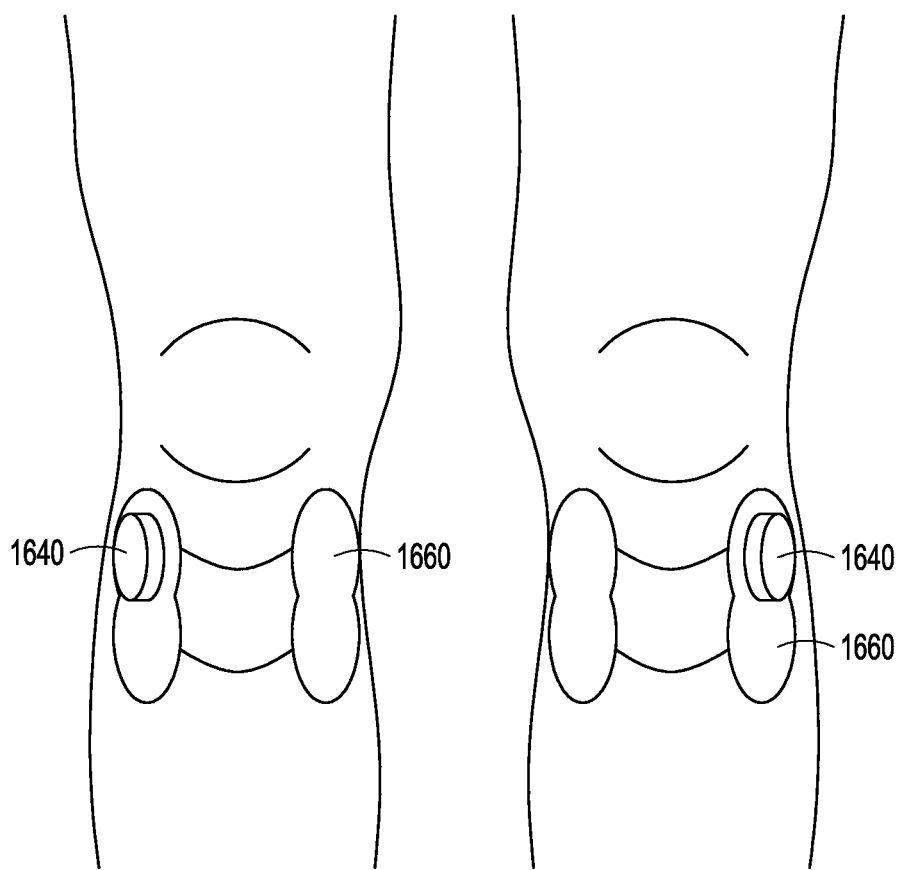
FIG. 16E shows an example of placement of the detachable adhesive patch of FIG. 16D, such as at a peroneal nerve target location, just below the knee on an anterior portion of the lower limb, with a detachable electronics unit.

FIG. 16E shows an example of placement of the detachable adhesive patch 1660 of FIG. 16D, such as at a peroneal nerve target location, just below the knee on an anterior portion of the lower limb, with the detachable electronics unit 1640 magnetically or otherwise attached to the detachable adhesive patch 1660.

Figure 16F:
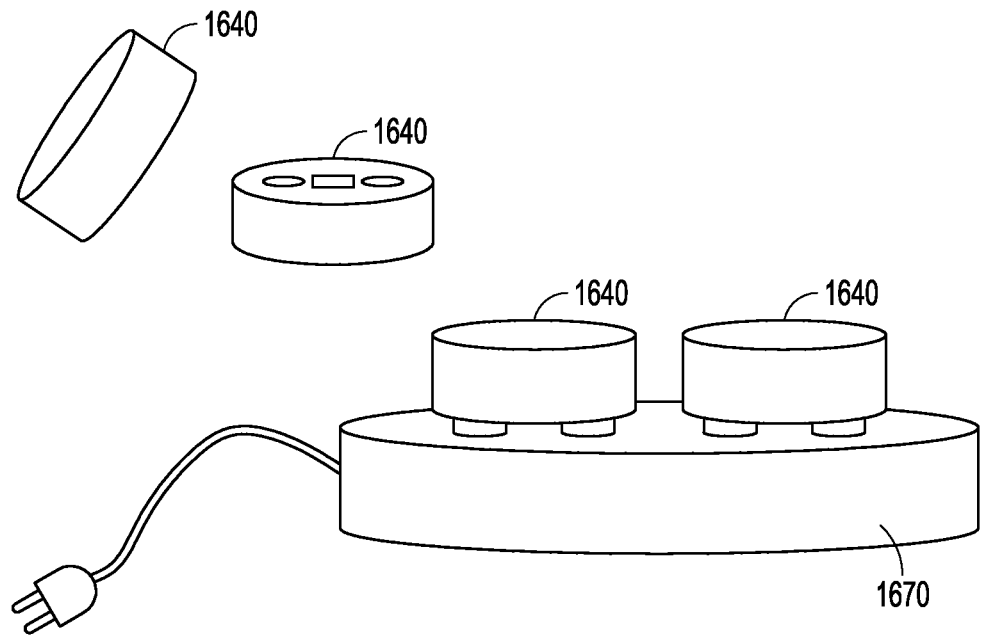
FIG. 16F shows an example of a local external interface device.

FIG. 16F shows an example of a local external interface device 1670, such as can be used for wirelessly or otherwise charging or re-charging one or more detachable electronics units 1640, such as by plugging into an AC wall outlet power source, or for communicating data wirelessly to or from the one or more detachable electronics units 1640, such as via Bluetooth to a mobile phone application, such as for further communication with a remote server.

Figure 16G:
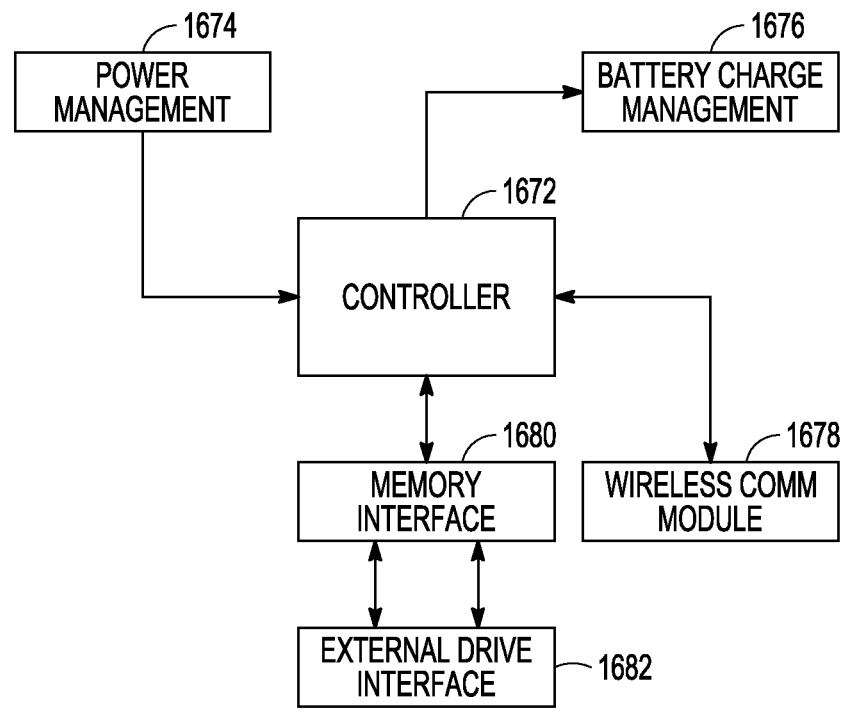
FIG. 16G shows an example of a block diagram of the local external interface device.

FIG. 16G shows an example of a block diagram of the local external interface device 1670. The local external interface device can include a controller circuit 1672, such as can interface with a power management circuit 1674, a battery charge management circuit 1676, a wireless communications transceiver circuit 1678, and a memory interface circuit 1680, such as can include or be coupled to an external memory drive interface circuit 1682. The power management circuit can include an AC/DC converter circuit, and a buck converter, boost converter, buck-boost converter, or other DC-DC power converter circuit, such as can generate an appropriate supply voltage for charging or re-charging the one or more electronics units 1640, such as via the battery charge management circuit 1676.

As an alternative to the selective recruitment of certain nerve fiber types using HF electrostimulation to stimulate GABA production, thereby calming RLS or PLMD leg twitching or motion symptoms, blocking conduction to the spinal cord of a target nerve (e.g., one or more of the peroneal, femoral, or sural nerves or one or more of their branches, or other nerve target) can be carried out to disrupt, inhibit, or calm RLS or other leg twitching or motion symptoms. For example, an AC waveform can be applied directly to the nerve using a cuff electrode wrapped around it, such as for applying an HF electrostimulation waveform thereto.

In an example of the present techniques, such a nerve conduction block can be achieved by transcutaneously modulating the desired high-frequency blocking signal onto a lower frequency carrier signal, such as to effectively block conduction of electrical signals along the nerve without requiring an implanted electrode or device.

Figure 17:
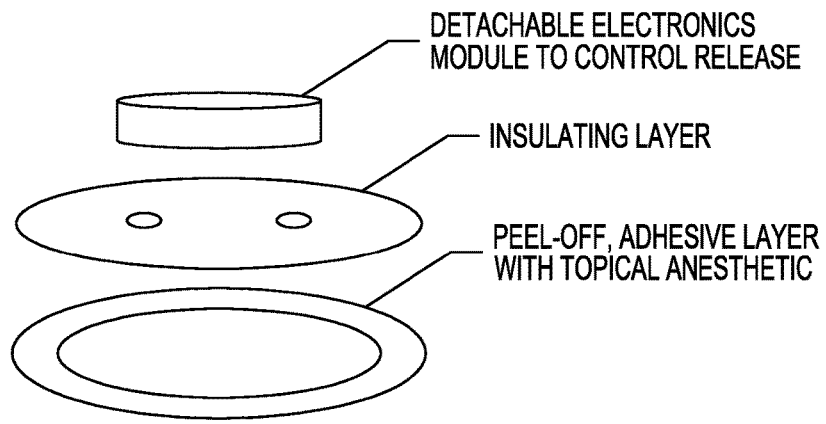
FIG. 17 illustrates an example of a transdermal chemical agent delivery adhesive patch.

FIG. 17 illustrates an example of a transdermal chemical agent delivery adhesive patch. In an example of the present techniques, conduction blocking can be obtained or assisted by applying a transdermal drug or chemical agent delivery adhesive patch with a topical anesthetic (e.g., lidocaine, bupivacaine, capasaicin), such as can be triggered to contact and permeate the skin, such as upon activation by an electrical trigger signal such as can be generated by on-board electronics that can be carried by the transdermal drug delivery adhesive patch. In the example of FIG. 17, the patch can include a most proximal peel-off adhesive layer, such as can include a topical anesthetic. A next more proximal layer can include an insulating layer, such as with cutouts to allow contact to electrodes controlling the release of the chemical agent. A more distal layer can include a detachable electronics module, such as can be configured to control release of the chemical agent, such as to block nerve conduction between the spinal cord and a target nerve location (e.g., one or more of the peroneal, femoral, or sural nerves or one or more of their branches, or other nerve target), such as to alleviate one or more RLS symptoms such as leg muscle twitching or motion.

Figure 18:
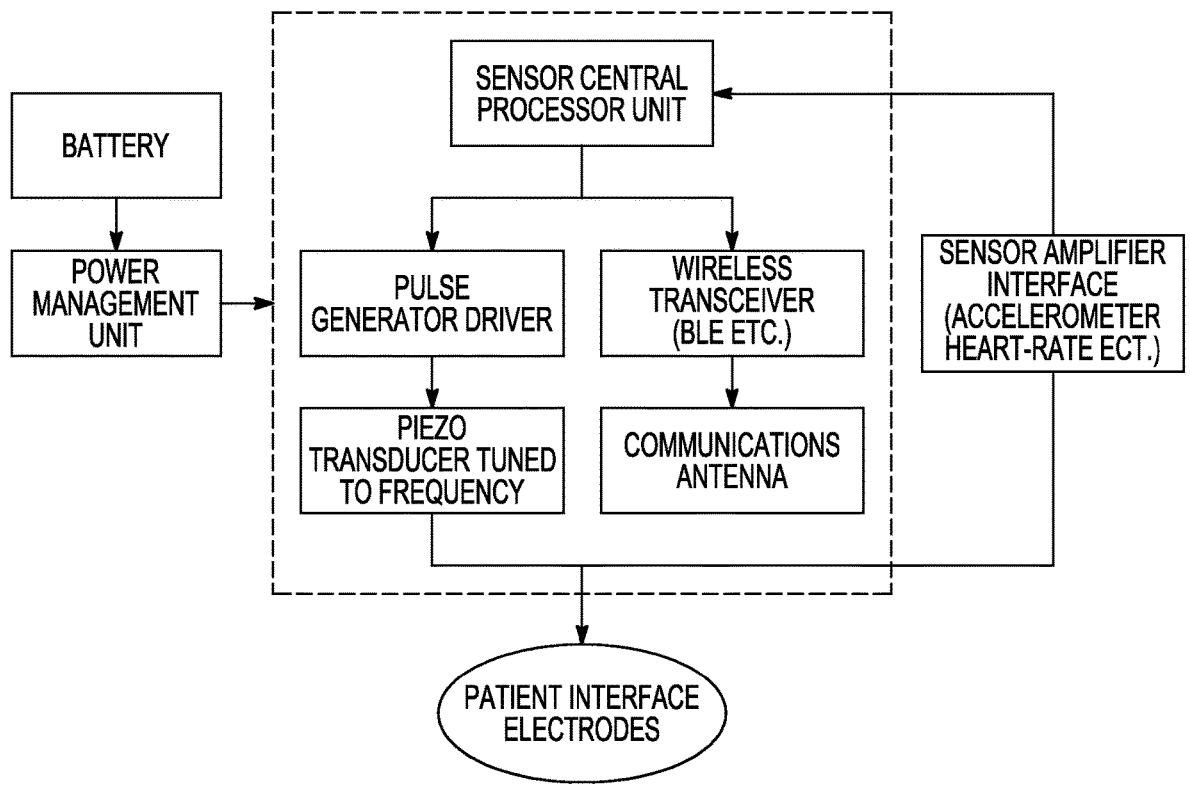
FIG. 18 shows an alternative closed-loop ultrasound embodiment, such as can provide ultrasound energy to one or more of the target nerve locations described herein (e.g., femoral nerve, peroneal nerve, or sural nerve).

FIG. 18 shows an alternative closed-loop ultrasound embodiment, such as can provide ultrasound energy to one or more of the target nerve locations described herein (e.g., femoral nerve, peroneal nerve, or sural nerve). In this example, electrical energy can be converted to ultrasound energy, such as using a piezoelectric transducer tuned to the ultrasound frequency, and driven by an ultrasound-frequency electrical pulse generator circuit.

In an example, ultrasound energy can be delivered to the target nerve locations in the subject in combination with the HF RLS electrostimulation described herein. In an example, nerve ablation (e.g., by RF heating or using a freezing agent) can be additionally or alternatively used to block nerve activity one or more of the target nerve locations described herein (e.g., femoral nerve, peroneal nerve, or sural nerve).

Figure 19A:
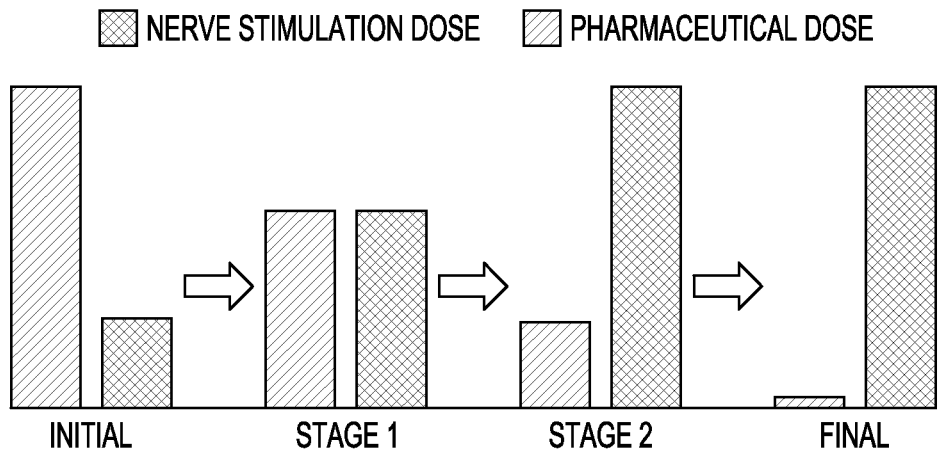
FIGS. 19A, 19B shows an example of a method of using the HF RLS electrostimulation therapy described herein in conjunction with pharmaceutical therapy.
Figure 19B:
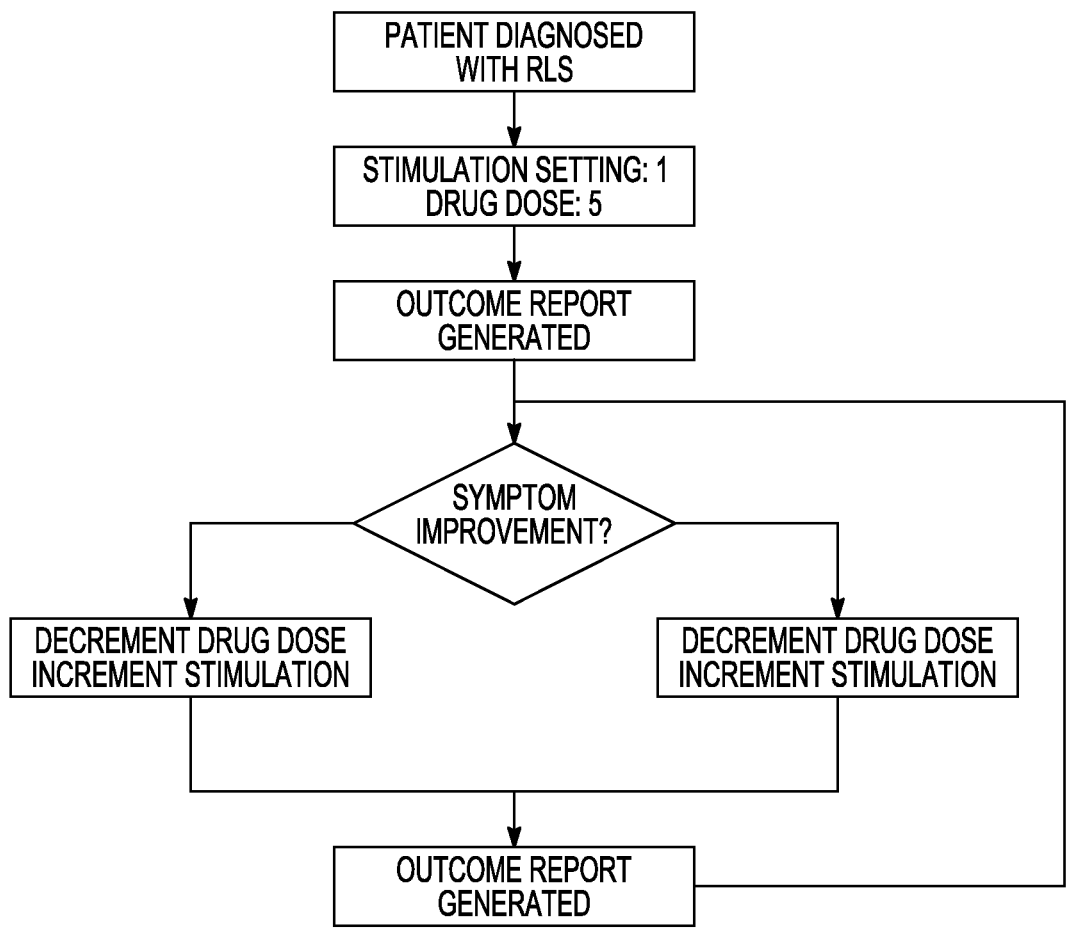

FIGS. 19A-19B shows an example of a method of using the HF RLS electrostimulation therapy described herein in conjunction with pharmaceutical therapy, such as to downwardly titrate the pharmaceutical therapy in stages as the HF RLS electrostimulation therapy is increased. In an example, this approach may be used to find an appropriate pharmaceutical treatment level that can avoid RLS augmentation or other pharmaceutical side effects, or to wean the subject of pharmaceutical treatment entirely.

Patients suffering from RLS may complain about symptoms that are or become present in the evenings or at bedtime, thereby preventing the patient from being able to fall asleep. Sleep onset latency can be defined as the amount of time taken to accomplish a transition from full wakefulness to sleep, such as to the lightest of non-REM sleep stage.

Patients with RLS can have extremely long sleep latencies, which can be improved using the therapies described herein.

As described herein, an actigraphic recording, a measure of sympathetic tone (such as heart rate or, particularly, of heart rate variability), a measure of sleep, such as an EEG, may be used to identify when the patient is awake, waking, asleep, or falling asleep, and used to trigger a therapy such as described herein to turn on and off appropriately, or to be adjusted to an appropriate level.

Figure 20:
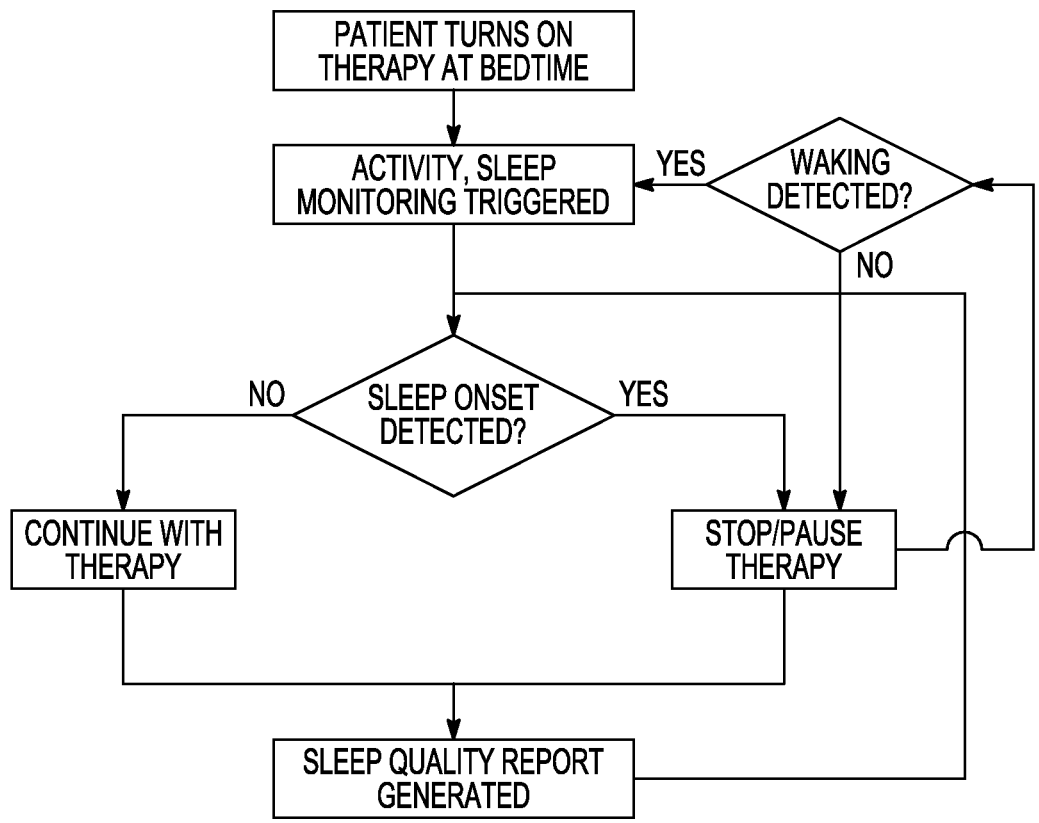
FIG. 20 shows an example of a technique that can be used to turn on and off the HF RLS electrostimulation therapy such as described herein.

FIG. 20 shows an example of a technique that can be used to turn on and off the HF RLS electrostimulation therapy such as described herein. The patient can turn on the therapy at bedtime, such as by actuating a switch or other user interface device. Activity and sleep monitoring can be triggered in addition to the therapy. If sleep onset is detected, then therapy can be stopped or paused, such as until waking is detected, at which time therapy can be resumed, with further monitoring of activity or sleep. If no sleep is detected, or if sufficient lower leg movement activity is detected, then therapy can be continued or increased. A sleep quality report can be generated, such as using information from the sleep detector, and which can include using information about the therapy delivered.

Adaptation of Nerves and Mitigation

Neurostimulation therapy can decrease in effectiveness over an extended period of time, especially when used continuously, such as can be the case for devices with implanted electrostimulation electrodes. Such a neural accommodation or tolerance can be attributed to neural reorganization (plasticity) or to attenuation of end organ responsiveness. Neural plasticity is the change of structure, function, and organization of neurons in response to a new experience. The present RLS electrostimulation therapy system and techniques can include certain features that can help make it less susceptible to such a decrease in efficacy over longer term chronic use.

First, the present RLS electrostimulation therapy system can be configured to be used only during periods of time when RLS symptoms present (e.g., usually no more than a few hours on one or several nights of the week). In an open-loop configuration, this can include using a timer, using a clock with time-of-day information, or both. In a closed-loop configuration, this can include using one or more sensors, such as described herein, such as to detect when RLS or PLMD symptoms are present, or to detect a physiological indicator indicating susceptibility to or aggravation of RLS or PLMD symptoms (e.g., over-assertion of sympathetic tone in a heart rate variability (HRV) or other indication of automatic balance), such as for controlling initiation, titration, or adjustment of electrostimulation therapy based on such sensor information, which can be used alone or in combination with the timer, the clock time-of-day information, or both. With the RLS electrostimulation exposure time being limited, there is limited window for neural accommodation owing to plasticity.

Second, the present RLS electrostimulation therapy system can have its controller circuit 1002 configured to provide waveform variability or adaptations, such as to help counter possible neural accommodation. This can include modulating one or more electrostimulation waveform parameters such as, for example, one or more of pulsewidth, amplitude, frequency, or burst-mode or inter-burst intervals.

Figure 21:
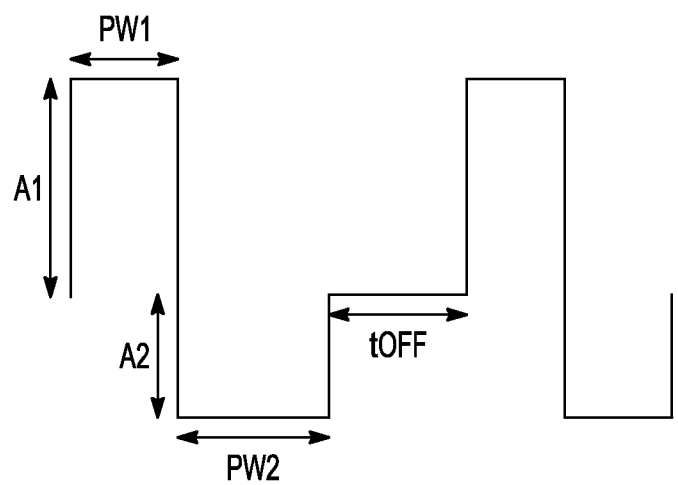
FIG. 21 shows an example a possible RLS electrostimulation waveform, such as can be generated by the present RLS electrostimulation therapy system.

FIG. 21 shows an example of possible RLS electrostimulation waveform, such as can be generated by the present RLS electrostimulation therapy system. One or more of the electrostimulation parameters can be varied, e.g., over time from an initial setting. Examples of electrostimulation parameters that can be set or adjusted can include, for the square wave electrostimulation waveform of FIG. 21, positive amplitude (A1), positive pulsewidth (PW1), negative amplitude (A2), negative pulsewidth (PW2), off time duration between successive electrostimulation pulses (tOFF).

Figure 22:
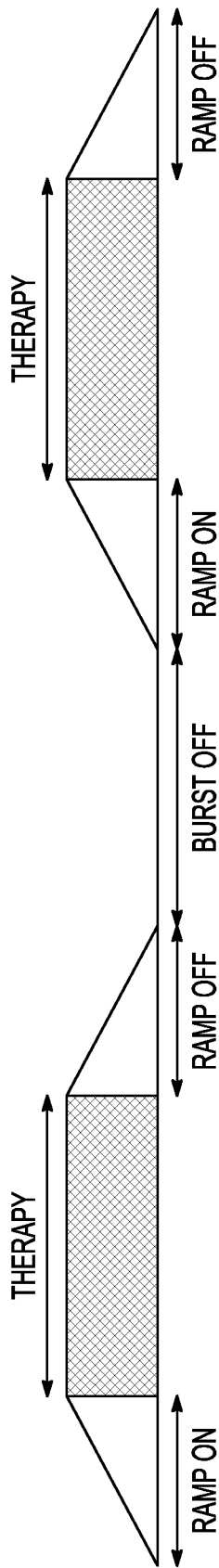
FIGS. 22 and 23 show examples of waveform patterns that are specifically configured to inhibit or prevent short-term neural accommodation
Figure 23:
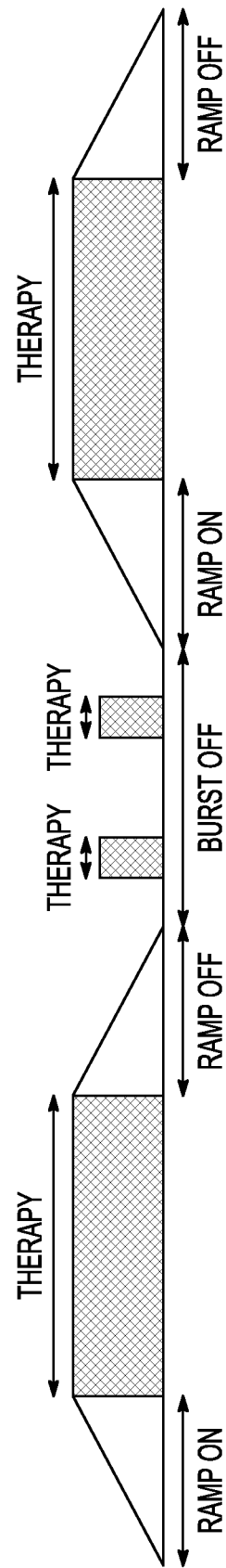

FIGS. 22 and 23 show examples of waveform patterns that are specifically configured to inhibit or prevent short-term neural accommodation. FIG. 22 shows a gradual ramp up (e.g., with ramping duration RampON) or ramp down (e.g., with ramping duration RampOFF), or both, of one or more (amplitude A1, A2, or both, or pulse-width PW1, PW2, or both) parameters until the desired therapeutic dosage has been reached, while maintaining charge-balanced electrostimulation, if desired. In addition to being useful to inhibit neural accommodation, ramp-up or ramp down can help further reduce or avoid sensory perception of the RLS therapy electrostimulation stimulus. The therapy stimuli waveforms may also be separated by an "off" period (BurstOFF) between bursts, such as shown in FIG. 22. This can help further reduce the exposure of any repeating pattern to the target nerve while still maintaining therapeutic efficacy.

FIG. 23 shows a technique by which the primary electrostimulation waveforms may be separated by "off" periods (BurstOFF), during which smaller secondary bursts of electrostimulation therapy can be applied, for example, as micro-bursts. The smaller secondary bursts of therapy can inject lesser charge into the nerve, such as by using a decreased amplitude, decreased pulse-width, or altered frequency.

Figure 24:
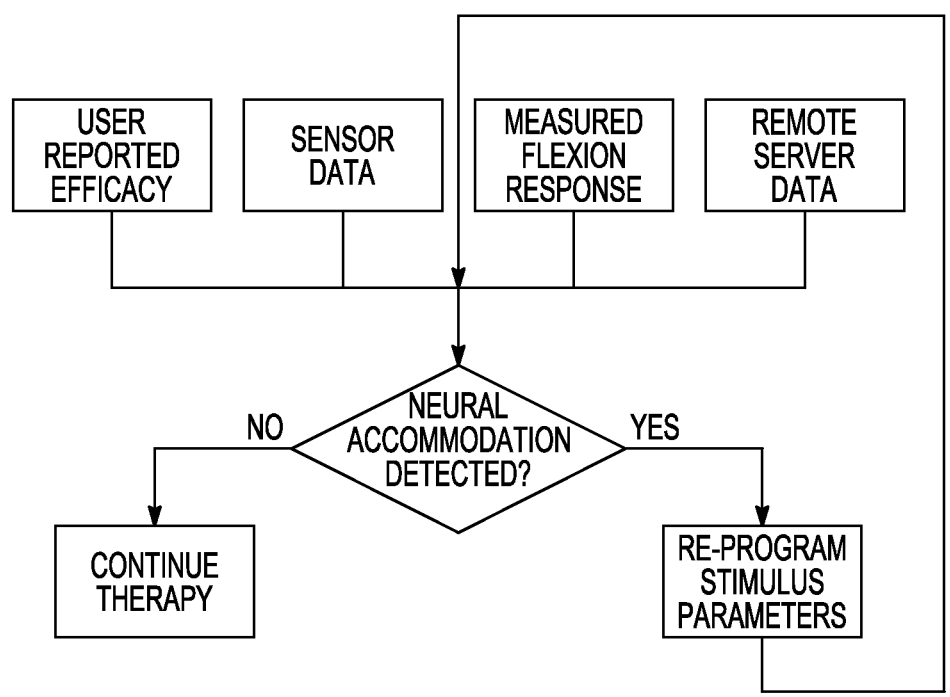
FIG. 24 is a flow chart showing an example of a technique for using flexion response information for establishing one or more RLS electrostimulation parameters, either initially, or recurrently, such as to help avoid neural accommodation or to help maintain subsensory therapy.

Additionally or alternatively, the RLS electrostimulation therapy waveform may also be varied, such as in a fixed frequency range around a center frequency (e.g., 4000 Hz) in each burst, such as to further reduce any perceived or detected accommodation-related decrease in therapeutic efficacy. These actions may be triggered by user input of RLS discomfort scores, or automatically, such as by the RLS electrostimulation system controller circuit reviewing collected sensor data indicating RLS or PLMD symptoms or related physiological factors, such as leg-movements, hours of use per night, amplitude settings, and reported IRLSS score improvements. The RLS electrostimulation waveform parameters may also be modified, such as to help ensure that there is a continued decrease in measured flexion response from the patient, such as to maintain subsensory RLS electrostimulation. For example, if the amplitude of the flexion response (Fr-III) increases over time with use of RLS electrostimulation therapy, one or more of the RLS electrostimulation therapy parameters may again be re-programmed, such as to help promote or ensure continued minimization of this flexion response, such as shown in FIG. 24. Additionally, or alternatively, an interferential current therapy approach can be used within the HF frequency range, such as to help inhibit, suppress, or prevent neural accommodation.

VARIOUS NOTES AND ASPECTS

Although the present description has referred to RLS and RLS therapy, including HF RLF electrostimulation therapy, the present techniques for detecting or treating RLS can also be applicable to PLMD, during which similar symptoms (leg twitching or motions) can occur during sleep.

A numbered non-limiting list of aspects of the present subject matter is presented below.

Aspect 1 can include or use subject matter (such as an apparatus, a system, a device, a method, a means for performing acts, or a device readable medium including instructions that, when performed by the device, can cause the device to perform acts), such as can include providing treatment of one or more symptoms associated with Restless Legs Syndrome (RLS) or Periodic Limb Movement Disorder (PLMD), such as can include using applied high-frequency electrostimulation. This can include locating at least one electrostimulation electrode at a location associated with at least one of, or at least one branch of, a sural nerve, a peroneal nerve, or a femoral nerve of a subject with RLS or PLMD. Electrostimulation can then be delivered to the location to help reduce or alleviate the one or more symptoms associated with RLS or PLMD.

Aspect 2 can include or use, or can optionally be combined with the subject matter of Aspect 1 to include or use delivering subsensory (e.g., not felt), subthreshold (e.g., muscles not activated), AC high frequency (HF) electrostimulation to the location, such as at a HF frequency that exceeds 500 Hz and is less than 15,000 Hz to help reduce or alleviate the one or more symptoms associated with RLS or PLMD.

Aspect 3 can include or use, or can optionally be combined with the subject matter of one or more of Aspects 1-2 such that the delivering electrostimulation includes delivering controlled-current electrostimulation.

Aspect 4 can include or use, or can optionally be combined with the subject matter of one or more of Aspects 1-3 such that delivering controlled-current electrostimulation includes delivering at a controlled current level that is between 5 milliamperes and 30 milliamperes.

Aspect 5 can include or use, or can optionally be combined with the subject matter of one or more of Aspects 1-4 such that delivering electrostimulation includes delivering charge-balanced AC electrostimulation. For example, this can include positive-going waveform portions delivering an amount of charge that is balanced out by negative-going waveform portions.

Aspect 6 can include or use, or can optionally be combined with the subject matter of one or more of Aspects 1-5, such as can include delivering electrostimulation is at a frequency that is between 4 kHz and 5 kHz.

Aspect 7 can include or use, or can optionally be combined with the subject matter of one or more of Aspects 1-6, such as can include delivering subsensory and subthreshold electrostimulation such as can be established at or adjusted to a level that is not felt by the subject and does not induce muscular contraction in the subject.

Aspect 8 can include or use, or can optionally be combined with the subject matter of one or more of Aspects 1-7, such that the delivering electrostimulation includes using a waveform to activate A-Beta fibers, e.g., preferentially over other nerve fiber types at the target nerve location.

Aspect 9 can include or use, or can optionally be combined with the subject matter of one or more of Aspects 1-8, such as can include delivering electrostimulation using a waveform that can be selected such as to activate A-Beta fibers (e.g., preferentially) such as to release GABA to help inhibit overactive A-Delta fibers, C fibers, or both.

Aspect 10 can include or use, or can optionally be combined with the subject matter of one or more of Aspects 1-9, such as can include delivering controlled-current electrostimulation such as using an energy level that or other electrostimulation characteristic value that can be established or adjusted based on a measured electrode-skin interface impedance.

Aspect 11 can include or use, or can optionally be combined with the subject matter of one or more of Aspects 1-10, such as can include using an electrostimulation waveform that can elicit a resulting measured compound action potential (CAP) having a higher amplitude ratio of A-Beta fiber to C fiber components recorded at a (e.g., peripherally extending) distance from the electrostimulation electrode along a targeted nerve or branch thereof, such as an associated one of a sural nerve, a peroneal nerve, or a femoral nerve, as compared to an amplitude ratio from a recorded response to a reference electrostimulation waveform having a frequency of 150 Hz.

Aspect 12 can include or use, or can optionally be combined with the subject matter of one or more of Aspects 1-11, such as can include delivering electrostimulation that can be established or adjusted, such as based on a measured load impedance or component (e.g., an electrode-skin interface impedance) thereof.

Aspect 13 can include or use, or can optionally be combined with the subject matter of one or more of Aspects 1-12, such as can include selecting or receiving a subject presenting with RLS or PLMD. Further, this can optionally include selecting the subject as not presenting with at least one of peripheral neuropathy or RLS augmentation, e.g., beyond the subject's legs.

Aspect 14 can include or use, or can optionally be combined with the subject matter of one or more of Aspects 1-13, such as can be triggered or adjusted automatically, such as in response to a sensor or other indication of an RLS symptom of the subject.

Aspect 15 can include or use, or can optionally be combined with the subject matter of one or more of Aspects 1-14, such as can include delivering electrostimulation that can be triggered or adjusted, such as automatically, such as in response to a sensor or other indication of an PLMD symptom of the subject.

Aspect 16 can include or use, or can optionally be combined with the subject matter of one or more of Aspects 1-15, such as can include delivering electrostimulation that can be triggered or adjusted, such as automatically, such as in response to time-of-day information (e.g., from a clock or timer circuit).

Aspect 17 can include or use, or can optionally be combined with the subject matter of one or more of Aspects 1-16, such as can include delivering electrostimulation that can be triggered or adjusted, such as automatically, such as in response to a sensor or other indication of posture of the subject.

Aspect 18 can include or use, or can optionally be combined with the subject matter of one or more of Aspects 1-17, such as can include delivering electrostimulation that can be triggered or adjusted, such as automatically, such as in response to a sensor or other indication of sleep status or sleep state of the subject.

Aspect 19 can include or use, or can optionally be combined with the subject matter of one or more of Aspects 1-18, such as can include delivering electrostimulation that can be triggered or adjusted, such as automatically, such as in response to a sensor or other indication of an autonomic balance of the subject (e.g., heart rate variability (HRV) or the like).

Aspect 20 can include or use, or can optionally be combined with the subject matter of one or more of Aspects 1-19, such as can include delivering electrostimulation that can be triggered or adjusted, such as automatically, such as in response to a sensor or other indication of one or more of leg or foot movement of the subject (e.g., from an accelerometer).

Aspect 21 can include or use, or can optionally be combined with the subject matter of one or more of Aspects 1-20, such as can include delivering electrostimulation that can be triggered or adjusted, such as automatically, such as in response to an indication of a drug therapy of the subject. For example, an RLS electrostimulation therapy treatment plan can gradually increase electrostimulation energy levels over a period of time that can be long enough to gradually decrease an RLS drug therapy to the subject.

Aspect 22 can include or use, or can optionally be combined with the subject matter of one or more of Aspects 1-21, such as can include using information about the delivered electrostimulation (or a physiological response to the delivered electrostimulation) to influence a drug therapy of the subject. For example, this can include delivering electrostimulation and measuring a flexion response or a compound action potential (CAP) response, and using such physiological response information to determine whether or how to titrate one or more drugs delivered to the patient.

Aspect 23 can include or use, or can optionally be combined with the subject matter of one or more of Aspects 1-22, such as can include communicating information about the delivered electrostimulation, its efficacy (e.g., such as a measured physiological parameter measured in association with providing therapy), or the one or more symptoms (e.g., leg movement, sleep status, or the like) to a local or remote external device (such as a local interface device or a remote server device).

Aspect 24 can include or use, or can optionally be combined with the subject matter of one or more of Aspects 1-23, such as can include locating an electrostimulation electrode at an external location associated with a sural nerve or at least one branch (e.g., directly connected peripherally extending) branch thereof.

Aspect 25 can include or use, or can optionally be combined with the subject matter of one or more of Aspects 1-24, such as can include locating an external electrostimulation electrode at a location associated with a peroneal nerve or at least one branch (e.g., directly connected peripherally extending) thereof.

Aspect 26 can include or use, or can optionally be combined with the subject matter of one or more of Aspects 1-25, such as can include locating an electrostimulation electrode at an external location associated with a femoral nerve or at least one branch (e.g., directly connected peripherally extending) thereof.

Aspect 27 can include or use, or can optionally be combined with the subject matter of one or more of Aspects 1-26, such as can include locating an electrostimulation electrode at an external location at or near a knee of the subject.

Aspect 28 can include or use, or can optionally be combined with the subject matter of one or more of Aspects 1-27, such as can include locating the electrostimulation electrode such as can include placing a knee sleeve about the subject's leg at the subject's knee.

Aspect 29 can include or use, or can optionally be combined with the subject matter of one or more of Aspects 1-28, such as can include locating the electrostimulation electrode at an external location at or near a heel of the subject.

Aspect 30 can include or use, or can optionally be combined with the subject matter of one or more of Aspects 1-29, such as can include locating the electrostimulation electrode at an external location at or near a peroneal nerve target below a patella and just below a tibial tuberosity on an anterior portion of the subject's lower limb.

Aspect 31 can include or use, or can optionally be combined with the subject matter of one or more of Aspects 1-30, such as can include delivering electrostimulation triggered in response to at least one of: an RLS or PLMD symptom, a time-of-day, a posture indication, a sleep-status indication, an autonomic balance indication, or a leg or foot movement indication.

Aspect 32 can include or use, or can optionally be combined with the subject matter of one or more of Aspects 1-31, such as can include transcutaneously delivering the electrostimulation via an external electrode located on the subject.

Aspect 33 can include or use, or can optionally be combined with the subject matter of one or more of Aspects 1-32, such as can include treating one or more symptoms associated with Restless Legs Syndrome (RLS) or Periodic Limb Movement Disorder (PLMD) using applied electrostimulation. This can include locating at least one electrostimulation electrode at a location associated with at least one of, or at least one branch of, a sural nerve, a peroneal nerve, or a femoral nerve. It can include delivering, subsensory, subthreshold, AC electrostimulation using a waveform configured to provide a resulting measured compound action potential (CAP) having an increased amplitude ratio of A-Beta fiber to C fiber components recorded at a distance from the electrostimulation electrode along an associated one of a sural nerve, a peroneal nerve, or a femoral nerve relative to a reference electrostimulation waveform at 150 Hz.

Aspect 34 can include or use, or can optionally be combined with the subject matter of one or more of Aspects 1-33, such as can include treating one or more symptoms associated with Restless Legs Syndrome (RLS) or Periodic Limb Movement Disorder (PLMD) using applied high-frequency electrostimulation. An electrostimulation electrode can be located at a location associated with at least one of, or at least one branch of, a sural nerve, a peroneal nerve, or a femoral nerve. A subsensory, subthreshold, AC electrostimulation can be delivered, such as using a waveform configured to release GABA, such as to provide a resulting higher measured increase in GABA relative to any increase in GABA elicited from a 150 Hz reference electrostimulation waveform.

Aspect 35 can include or use, or can optionally be combined with the subject matter of one or more of Aspects 1-34, such as can include or use a device for treating one or more symptoms associated with Restless Legs Syndrome (RLS) or Periodic Limb Movement Disorder (PLMD) using high-frequency electrostimulation. The device can include or be coupled to external electrostimulation electrodes, such as can be configured to be affixed to a subject such as at a location associated with at least one of, or at least one branch (e.g., directly connected peripherally or distally extending branch) of, a sural nerve, a peroneal nerve, or a femoral nerve to deliver electrostimulation thereto. An electrostimulation generator circuit can be adapted to be coupled to the electrostimulation electrodes to generate the electrostimulation for delivery by the electrostimulation electrodes. A controller circuit can be coupled to the electrostimulation generator circuit, such as to control at least one parameter of the electrostimulation.

Aspect 36 can include or use, or can optionally be combined with the subject matter of one or more of Aspects 1-35, such as can include or use the electrostimulation generator circuit including a subsensory, subthreshold, AC electrostimulation generator circuit, adapted to be coupled to electrostimulation electrodes to deliver electrostimulation at the location at a frequency that exceeds 500 Hz and is less than 15,000 Hz to the location such as to help reduce or alleviate the one or more symptoms associated with RLS or PLMD.

Aspect 37 can include or use, or can optionally be combined with the subject matter of one or more of Aspects 1-36, such as can include or use the electrostimulation generator circuit having a controlled current circuit such as can be configured to control electrostimulation current such as at a current level that is between 5 milliamperes and 30 milliamperes.

Aspect 38 can include or use, or can optionally be combined with the subject matter of one or more of Aspects 1-37, such as can include or use the electrostimulation generator circuit being configured to provide a controlled current electrostimulation waveform such as having a frequency that is between 4 kHz and 5 kHz.

Aspect 39 can include or use, or can optionally be combined with the subject matter of one or more of Aspects 1-38, such as can include or use a stabilizer such as to hold at least a portion of the device at a target location.

Aspect 40 can include or use, or can optionally be combined with the subject matter of one or more of Aspects 1-39, such as can include or use the stabilizer including a skin patch configured to adhere to the subject at the location for delivering electrostimulations thereto.

Aspect 41 can include or use, or can optionally be combined with the subject matter of one or more of Aspects 1-40, such as can include or use a stabilizer including a wearable sleeve that can be configured to hold the device at the location for delivering electrostimulations thereto.

Aspect 42 can include or use, or can optionally be combined with the subject matter of one or more of Aspects 1-41, such as can include or use a user-interface, such as can be coupled to the controller circuit such as to trigger or adjust electrostimulation such as in response to at least one of: an RLS or PLMD symptom, a time-of-day, a posture indication, a sleep-status indication, an autonomic balance indication, or a leg or foot movement indication.

Aspect 43 can include or use, or can optionally be combined with the subject matter of one or more of Aspects 1-42, such as can include or use a sensor that can be coupled to the controller circuit such as to trigger or adjust electrostimulation such as in response to at least one of: an RLS or PLMD symptom, a time-of-day, a posture indication, a sleep-status indication, an autonomic balance indication, or a leg or foot movement indication.

Aspect 44 can include or use, or can optionally be combined with the subject matter of one or more of Aspects 1-43, such as can include or use an accelerometer such as can be configured to detect movement of at least a portion of the subject (e.g., leg or foot movement).

Aspect 45 can include or use, or can optionally be combined with the subject matter of one or more of Aspects 1-44, such as can include or use the sensor including a clock circuit such as to provide a time-of-day indication.

Aspect 46 can include or use, or can optionally be combined with the subject matter of one or more of Aspects 1-45, such as can include or use a posture sensor such as can be configured to detect a posture (e.g., upright, recumbent, or the like) of the subject.

Aspect 47 can include or use, or can optionally be combined with the subject matter of one or more of Aspects 1-46, such as can include or use a sleep sensor configured to indicate a sleep status of the subject.

Aspect 48 can include or use, or can optionally be combined with the subject matter of one or more of Aspects 1-47, such as can include or use the sensor including an automatic balance indicator such as can be configured to provide information about at least one of a sympathetic tone or a parasympathetic tone of the subject.

Aspect 49 can include or use, or can optionally be combined with the subject matter of one or more of Aspects 1-48, such as can include or use the sensor including an impedance sensor such as can be configured to provide information about an impedance of or associated with the subject to the controller circuit such as for adjusting a parameter of the electrostimulation in response thereto.

Aspect 50 can include or use, or can optionally be combined with the subject matter of one or more of Aspects 1-49, such as can include or use the controller circuit being configured to use information about a drug therapy of the subject such as to initiate or adjust a parameter of the electrostimulation.

Aspect 51 can include or use, or can optionally be combined with the subject matter of one or more of Aspects 1-50, such as can include or use a transceiver circuit such as can be configured to communicate information such as about the delivered electrostimulation, its efficacy, one or more physiological parameters, or the one or more symptoms to a local or remote external device.

Aspect 52 can include or use, or can optionally be combined with the subject matter of one or more of Aspects 1-51, such as can include or use the electrostimulation electrodes being carried on an adhesive patch.

Aspect 53 can include or use, or can optionally be combined with the subject matter of one or more of Aspects 1-52, such as can include or use the adhesive patch being configured for a single use before disposing of the patch.

Aspect 54 can include or use, or can optionally be combined with the subject matter of one or more of Aspects 1-53, such as can include or use the device further including electronic circuitry or a battery also carried by the adhesive patch.

Aspect 55 can include or use, or can optionally be combined with the subject matter of one or more of Aspects 1-54, such as can include or use a device for treating one or more symptoms associated with Restless Legs Syndrome (RLS) or Periodic Limb Movement Disorder (PLMD) using electrostimulation at a sural nerve location posterior and inferior to an ankle malleolus of a human subject. The device can include or use a wearable adhesive patch, including external electrostimulation electrodes, such as can be configured to be affixed to a subject at the sural nerve location, and such as can include electrical contacts in a first arrangement for receiving signals from an electrostimulation electronics unit that is user-attachable and user-detachable from the patch.

Aspect 56 can include or use, or can optionally be combined with the subject matter of one or more of Aspects 1-55, such as can include or use the patch being sized and shaped to fit on a lateral side of a foot between the ankle malleolus and a heel of the human subject.

Aspect 57 can include or use, or can optionally be combined with the subject matter of one or more of Aspects 1-56, such as can include or use the patch including a central lobe for receiving the electrostimulation electronics unit (and optionally additionally carrying an electrostimulation electrode), and a plurality of wings extending from the central lobe such as to carry respective electrostimulation electrodes for contacting skin of the subject.

Aspect 58 can include or use, or can optionally be combined with the subject matter of one or more of Aspects 1-57, such as can include or use the electrostimulation electronics unit, such as can include electrical contacts in a second arrangement that matches the first arrangement of the patch.

Aspect 59 can include or use, or can optionally be combined with the subject matter of one or more of Aspects 1-58, such as can include or use one or more of the electrical contacts of the patch being magnetized such as to attract similarly arranged contacts of the electrostimulation electronics unit.

Aspect 60 can include or use, or can optionally be combined with the subject matter of one or more of Aspects 1-59, such as can include or use the patch including: a lower layer carrying hydrogel electrodes; an upper layer, including electrical contacts for interfacing with the electronics unit; and an intermediate layer, providing electrical connections to the hydrogel electrodes carried by the lower layer and to the electrical contacts included in the upper layer.

Aspect 61 can include or use, or can optionally be combined with the subject matter of one or more of Aspects 1-60, such as can include or use a device for treating one or more symptoms associated with Restless Legs Syndrome (RLS) or Periodic Limb Movement Disorder (PLMD) using electrostimulation at a peroneal nerve location inferior to a patella and to a tibial tuberosity on an anterior portion of a lower limb of a human subject. The device can include or use a wearable adhesive patch, such as including external electrostimulation electrodes, such as can be configured to be affixed to a subject at the peroneal nerve location, and including electrical contacts in a first arrangement such as for receiving signals from an electrostimulation electronics unit that is user-attachable and user-detachable from the patch.

Aspect 62 can include or use, or can optionally be combined with the subject matter of one or more of Aspects 1-61, such as can include or use a wearable adhesive patch includes electrodes at respective ends of the patch for placement on opposing lateral and medial locations across the tibia, and wherein the electrical contacts in the first arrangement are located at one of the ends of the patch.

Aspect 63 can include or use, or can optionally be combined with the subject matter of one or more of Aspects 1-62, such as can include or use the wearable adhesive patch including or using a return electrode such as can be arranged to be positioned anterior to the tibia when an electrode at one of the ends of the patch is placed laterally or medially over a peroneal nerve target.

Aspect 64 can include or use, or can optionally be combined with the subject matter of one or more of Aspects 1-63, such as can include or use the patch including lobes extending in opposing directions at each end of the patch, each lobe carrying an electrode.

Aspect 65 can include or use, or can optionally be combined with the subject matter of one or more of Aspects 1-64, such as can include or use the patch including or using: a lower layer carrying hydrogel electrodes; an upper layer, including electrical contacts for interfacing with the electronics unit; and an intermediate layer, providing electrical connections to the hydrogel electrodes carried by the lower layer and to the electrical contacts included in the upper layer.

Aspect 66 can include or use, or can optionally be combined with the subject matter of one or more of Aspects 1-65, such as can include or use a device for treating one or more symptoms associated with Restless Legs Syndrome (RLS) or Periodic Limb Movement Disorder (PLMD) using electrostimulation at a femoral nerve location anterior to a superior portion of a femur of a human subject. The device can include or use a wearable adhesive patch, including external electrostimulation electrodes, configured to be affixed to a subject at the peroneal nerve location, and including electrical contacts in a first arrangement for receiving signals from an electrostimulation electronics unit that is user-attachable and user-detachable from the patch.

Aspect 67 can include or use, or can optionally be combined with the subject matter of one or more of Aspects 1-66, such as can include or use the wearable adhesive patch including electrodes at respective ends of the patch for placement on opposing lateral and medial locations across the femur, and wherein the electrical contacts in the first arrangement are located at one of the ends of the patch.

Aspect 68 can include or use, or can optionally be combined with the subject matter of one or more of Aspects 1-67, such as can include or use the wearable adhesive patch including an return electrode arranged to be positioned anterior to the femur when an electrode at one of the ends of the patch is placed laterally or medially over a femoral nerve target.

Aspect 69 can include or use, or can optionally be combined with the subject matter of one or more of Aspects 1-68, such as can include or use the patch including lobes extending in opposing directions at each end of the patch, each lobe carrying an electrode.

Aspect 70 can include or use, or can optionally be combined with the subject matter of one or more of Aspects 1-69, such as can include or use the patch including: a lower layer carrying hydrogel electrodes; an upper layer, including electrical contacts for interfacing with the electronics unit; and an intermediate layer, providing electrical connections to the hydrogel electrodes carried by the lower layer and to the electrical contacts included in the upper layer.

The above description includes references to the accompanying drawings, which form a part of the detailed description. The drawings show, by way of illustration, specific embodiments in which the invention can be practiced. These embodiments are also referred to herein as "aspects" or "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of treating one or more symptoms associated with Restless Legs Syndrome (RLS) or Periodic Limb Movement Disorder (PLMD) using applied high-frequency electrostimulation, the method comprising:
locating at least one electrostimulation electrode at a location associated with at least one of, or at least one branch of, a sural nerve, a peroneal nerve, or a femoral nerve of a subject with RLS or PLMD; and
delivering electrostimulation to the location to help reduce or alleviate the one or more symptoms associated with RLS or PLMD, wherein the delivering electrostimulation includes delivering subthreshold electrostimulation to the location including using a high-frequency (HF) signal that exceeds 500 Hz and is less than 15,000 Hz.

2. The method of claim 1, wherein HF signal is modulated onto a lower frequency.

3. The method of claim 1, wherein the delivering electrostimulation includes delivering charge-balanced AC controlled-current electrostimulation at a controlled current level that is between 5 milliamperes and 30 milliamperes.

4. The method of claim 1, wherein the delivering electrostimulation is at a frequency that is between 4 kHz and 5 kHz.

5. The method of claim 1, wherein delivering electrostimulation includes delivering controlled-current electrostimulation that is established or adjusted based on a measured load impedance or component thereof.

6. The method of claim 1, wherein delivering electrostimulation includes using an electrostimulation waveform providing a resulting measured compound action potential (CAP) having a higher amplitude ratio of A-Beta fiber to C fiber components recorded at a distance from the electrostimulation electrode along an associated one of a sural nerve, a peroneal nerve, or a femoral nerve, as compared to a reference electrostimulation waveform having a frequency of 150 Hz.

7. The method of claim 1, wherein the delivering electrostimulation is triggered or adjusted automatically at least in part based on at least one of:
a sensor or other indication of sleep status or sleep state or sleep position of the subject; and
a sensor or other indication of leg or foot movement of the subject.

8. The method of claim 1, wherein the delivering electrostimulation includes delivering subsensory, subthreshold electrostimulation to the location.

9. The method of claim 1, wherein the delivering electrostimulation includes delivering electrostimulation to the location using a waveform to target A-Beta fibers for activation to help inhibit overactive at least one of A-Delta and C fibers.

10. The method of claim 1, wherein the delivering the electrostimulation produces a change in a flexion response.

11. The method of claim 1, wherein the locating an electrostimulation electrode is at an external location associated with a sural nerve or at least one branch thereof.

12. The method of claim 1, wherein the locating an external electrostimulation electrode is at an external location associated with a peroneal nerve or at least one branch thereof.

13. The method of claim 1, wherein the locating an electrostimulation electrode is at an external location associated with a femoral nerve or at least one branch thereof.

14. The method of claim 1, wherein the locating an electrostimulation electrode is at an external location at or near a knee of the subject.

15. The method of claim 1, wherein the locating the electrostimulation electrode is at an external location at or near a heel of the subject.

16. The method of claim 1, wherein the locating the electrostimulation electrode is at an external location at or near a peroneal target below a patella and below a tibial tuberosity on an anterior portion of the subject's lower limb.

17. An external device for treating one or more symptoms associated with Restless Legs Syndrome (RLS) or Periodic Limb Movement Disorder (PLMD) using high-frequency electrostimulation, the device comprising:
- external electrostimulation electrodes, configured to be affixed to a subject at a location associated with at least one of, or at least one branch of, a sural nerve, a peroneal nerve, or a femoral nerve to deliver electrostimulation thereto;
- an electrostimulation generator circuit, adapted to be coupled to the electrostimulation electrodes to generate the electrostimulation for delivery by the electrostimulation electrodes; and
- a controller circuit, coupled to the electrostimulation generator circuit, to control at least one parameter of the electrostimulation, wherein the electrostimulation includes a subthreshold electrostimulation for delivery to the location using a waveform including a high-frequency (HF) signal that exceeds 500 Hz and is less than 15,000 Hz.

18. The device of claim 17, wherein the HF signal is modulated onto a lower frequency.

19. The device of claim 17, wherein the electrostimulation generator circuit includes a controlled current circuit configured to control electrostimulation current at a current level that is between 5 milliamperes and 30 milliamperes.

20. The device of claim 17, wherein the electrostimulation generator circuit is configured to provide a controlled current electrostimulation waveform having a frequency that is between 4 kHz and 5 kHz.

21. The device of claim 17, further including a stabilizer to hold at least a portion of the device at the location, wherein the stabilizer includes at least one of a skin patch configured to adhere to the subject at the location for delivering electrostimulations thereto, a removable knee sleeve, compression shorts, compression leggings, a compression knee brace, or a knee sleeve.

22. The device of claim 17, including a sensor coupled to the controller circuit to trigger or adjust electrostimulation based at least in part on a sleep status or sleep state or sleep position or indication of leg or foot movement of the subject.

23. The device of claim 17, comprising an impedance sensor configured to provide information about an impedance associated with the subject to the controller circuit for adjusting a parameter of the electrostimulation in response thereto.

24. The device of claim 17, including a wearable adhesive patch, including external electrostimulation electrodes, configured to be affixed to a subject at the location, and including electrical contacts in a first arrangement for receiving signals from an electrostimulation electronics unit that is user-attachable and user-detachable from the patch.

25. The device of claim 17, the electrostimulation electrodes configured to deliver a subthreshold electrostimulation to the location using a waveform to target A-Beta fibers for activation to help inhibit overactive at least one of A-Delta and C fibers.

26. A device for treating one or more symptoms associated with Restless Legs Syndrome (RLS) or Periodic Limb Movement Disorder (PLMD) using applied high-frequency electrostimulation, the device comprising:
- means for locating at least one electrostimulation electrode at a location associated with at least one of, or at least one branch of, a sural nerve, a peroneal nerve, or a femoral nerve of a subject with RLS or PLMD for delivering electrostimulation to the location to help reduce or alleviate the one or more symptoms associated with RLS or PLMD, wherein the delivering electrostimulation includes delivering subthreshold electrostimulation to the location at a high-frequency (HF) frequency that exceeds 500 Hz and is less than 15,000 Hz to help reduce or alleviate the one or more symptoms associated with RLS or PLMD.

27. The device of claim 26, further comprising an external electrostimulation generator circuit configured for generating an electrostimulation waveform including the HF frequency.

* * * * *